US011299760B2

(12) United States Patent
Pande et al.

(10) Patent No.: US 11,299,760 B2
(45) Date of Patent: *Apr. 12, 2022

(54) USE OF MONENSIN TO REGULATE GLYCOSYLATION OF RECOMBINANT PROTEINS

(71) Applicant: Amgen Inc., Thousand Oaks, CA (US)

(72) Inventors: Sandhya Pande, Auburn, WA (US); Mirna Mujacic, Seattle, WA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/464,115

(22) Filed: Sep. 1, 2021

(65) Prior Publication Data

US 2021/0395793 A1 Dec. 23, 2021

Related U.S. Application Data

(63) Continuation of application No. 15/033,559, filed as application No. PCT/US2014/063211 on Oct. 30, 2014, now Pat. No. 11,130,980.

(60) Provisional application No. 61/898,310, filed on Oct. 31, 2013.

(51) Int. Cl.
 *C12P 21/00* (2006.01)
(52) U.S. Cl.
 CPC ................... *C12P 21/005* (2013.01)
(58) Field of Classification Search
 None
 See application file for complete search history.

(56) References Cited

U.S. PATENT DOCUMENTS

| | | | |
|---|---|---|---|
| 4,968,607 | A | 11/1990 | Dower et al. |
| 5,075,222 | A | 12/1991 | Hannum et al. |
| 5,149,792 | A | 9/1992 | Thomason |
| 5,272,064 | A | 12/1993 | Thomason |
| 5,395,760 | A | 3/1995 | Smith et al. |
| 5,610,279 | A | 3/1997 | Brockhaus et al. |
| 5,672,502 | A | 9/1997 | Birch et al. |
| 5,767,064 | A | 6/1998 | Sims et al. |
| 5,856,296 | A | 1/1999 | Mosley et al. |
| 5,877,293 | A | 3/1999 | Adair et al. |
| 5,886,152 | A | 3/1999 | Nakatani et al. |
| 5,981,713 | A | 11/1999 | Colotta et al. |
| 6,015,938 | A | 1/2000 | Boyle et al. |
| 6,054,297 | A | 4/2000 | Carter et al. |
| 6,096,728 | A | 8/2000 | Collins et al. |
| 6,235,883 | B1 | 5/2001 | Jakobovits et al. |
| 6,271,349 | B1 | 8/2001 | Dougall et al. |
| 6,337,072 | B1 | 1/2002 | Ford et al. |
| 6,544,424 | B1 | 4/2003 | Shevitz |
| 6,696,245 | B2 | 2/2004 | Winter et al. |
| 6,846,634 | B1 | 1/2005 | Tomlinson et al. |
| 8,053,238 | B2 | 11/2011 | Jin et al. |
| 9,481,901 | B2 | 11/2016 | Huang |
| 2003/0039958 | A1 | 2/2003 | Holt et al. |
| 2004/0009507 | A1 | 1/2004 | Winter et al. |
| 2004/0038291 | A2 | 2/2004 | Tomlinson et al. |
| 2004/0202995 | A1 | 10/2004 | De Wildt et al. |
| 2005/0202512 | A1 | 9/2005 | Tomlinson et al. |

FOREIGN PATENT DOCUMENTS

| | | |
|---|---|---|
| AU | 588819 B2 | 9/1989 |
| EP | 0367566 A1 | 5/1990 |
| EP | 0460846 B1 | 2/2002 |
| WO | 1994/10308 A1 | 5/1994 |
| WO | 1994/28391 A1 | 12/1994 |
| WO | 1997/01633 A1 | 1/1997 |
| WO | 2001/36637 A1 | 5/2001 |
| WO | 2008/154014 A2 | 12/2008 |
| WO | 2012/145682 A1 | 10/2012 |

OTHER PUBLICATIONS

Alessandri, L et al., "Increased serum clearance of oligomannose species present on a human IgG1 molecule", mAbs, vol. 4, No. 4, Jul. 1, 2012, pp. 509-520.
Ahn et al., Effect of culture temperature on erythropoietin production and glycosylation in a perfusion culture of recombinant CHO cells, *Biotechnol Bioeng* (2008) 101(6):1234-1244.
Bird et al., Single-chain antigen-binding proteins, *Science* (1988) 242:423-426.
Brasel et al., Hematologic effects of flt3 ligand in vivo in mice, *Blood* (1996) 88(6):2004-2012.
Catapano et al., Bioreactor design and scale-up in cell and tissue reaction engineering: principles and practice in *Cell and Tissue Reaction Engineering: Principles and Practice*; R. Eible et al, ed.(2009) 173-259 Springer-Verlag (Berlin/Heidelberg).
Chatterjee et al., Effect of monensin on Mason-Pfizer monkey virus glycoprotein synthesis, *J Virol* (1982) 44(3): 1003-1012.
Chothia et al., Canonical structures for the hypervariable regions of immunoglobulins, *J Mol. Biol* (1987) 196:901-917.
Chothia et al., Conformations of immunoglobulin hypervariable regions, *Nature* (1989) 342:877-883.
Do et al., Mechanism of BLyS action in B cell immunity, *Cytokine Growth Factor Rev.* (2002) 13(1):19-25.
Fukao et al., Effect of monensin on secretion of t-pa from melanoma (Bowes), *Cell Structure and Function* (1989) 14:673-684.
Furey, Scale-up of a cell culture perfusion process, *Gen Eng News* (2002) 22(7):62-63.
Goetze et al, High-mannose glycans on the Fc region of therapeutic IgG antibodies increase serum clearance in humans, *Glycobiology* (2011) 21(7):949-959.
Hakannson et al., Crystal structure of the trimeric α-helical coiled-coil and the three lectin domains of human lung surfactant protein D, *Structure* (1999) 7:255-264.
Harbury et al., A switch between two-, three-, and four-stranded coiled coils in gcn4 leucine zipper mutants, *Science* (1993) 262:1401-1405.
Harbury et al., Crystal structure of an isoleucine-zipper trimer, *Nature* (1994) 371:80-83.

(Continued)

*Primary Examiner* — Michail A Belyavskyi
(74) *Attorney, Agent, or Firm* — Henry P. Wu

(57) ABSTRACT

Methods of modulating the properties of a cell culture expressing a protein of interest are provided. In various embodiments the methods relate to the addition of cell-cycle inhibitors to growing cell cultures.

10 Claims, 7 Drawing Sheets

(56) References Cited

OTHER PUBLICATIONS

Hollinger et al., "Diabodies": Small bivalent and bispecific antibody fragments, *Proc Natl Acad Sci USA* (1993) 90:6444-6448.
Honegger et al., Yet another numbering scheme for immunoglobulin variable domains : an automatic modeling and analysis tool, *J Mol Biol* (2001) 309:657-670.
Huston et al., Protein engineering of antibody binding sites: Recovery of specific activity in an anti-digoxin single-chain Fv analogue produced in *Escherichia coli*, *Proc Natl Acad Sci USA* (1988) 85:5879-5883.
Kaufman et al , Synthesis, processing, and secretion of recombinant human factor viii expressed in mammalian cells, *J Biol Chem* (1988) 263:6352-6362.
Kaufman, Selection and Coamplification of Heterologous Genes in Mammalian Cells, *Meth Enzymol* (1999) 185:537-566.
Korndorfer et al., Crystallographic analysis of an "anticalin" with tailored specificity for fluorescein reveals high structural plasticity of the lipocalin loop region, *Proteins: Structure, Function, and Bioinformatics* (2003) 53(1):121-129.
Kousoulas et al., Effect of the ionophore monensin on herpes simplex virus type 1-induced cell fusion, glycoprotein synthesis, and virion infectivity, *Intervirology* (1983) 20:56-60.
Kubo et al., Expression of membrane IGM by a human B lymphoblastoid cell line in the presence of monensin, *Mol Immunol* (1983) 20(3):345-348.
Kuhn et al., Effect of monensin on synthesis, post-translational processing, and secretion of dopamine β-hydroxylase from PC12 pheochromocytoma cells, *J Biol Chem* (1986) 261(8):3816-3825.
Kuystermans et al., Bioreactor systems for producing antibody from mammalian cells in antibody expression and production, *Cell Engineering* (2011) 7:25-52.
Ledger P. W. et al, Abnormal Glycosylation of Human Fibronectin Secreted in the Presence of Monensin, The Journal of Biological Chemistry Abnormal Glycosylation of Human Fibronectin Secreted in the Presence of Monensin* vol. 258, No. 1, Jan. 10, 1983).
Lovejoy et al., Crystal structure of a synthetic triple-stranded α-helical bundle, *Science* (1993) 259:1288-1293.
Machamer et al., Monensin prevents terminal glycosylation of the N- and O-linked oligosaccharides of the HLA-DR-associated invariant chain and inhibits its dissociation from the alpha-beta chain complex, *Proc Natl Acad Sci USA* (1984) 81:1287-1291.
Maisonpierre et al., Angiopoietin-2, a natural antagonist for Tie2 that disrupts in vivo angiogenesis, *Science* (1997) 277(5322):55-60.
McKinnon et al., Expression, purification and characterization of secreted recombinant human insulin-like growth factor-I (IGF-I) and the potent variant des(1-3)IGF-I in Chinese hamster ovary cells, *J. Mol Endocrinol* (1999) 6:231-239.

Milstein et al., Hybrid hybridomas and their use in immunohistochemistry, *Nature* (1983) 537:3053.
Pacis et al., Effects of cell culture conditions on antibody n-linked glycosylation—what affects high mannose 5 glycoform, *Biotechnol Bioeng* (2011) 108:2348-2358.
Park et al., Monensin inhibits the growth of renal cell carcinoma cells via cell cycle arrest or apoptosis, *Int J Oncol*, (2003) 22(4):855-860.
Park et al., Monensin-mediated growth inhibition in human lymphoma cells through cell cycle arrest apoptosis, *Br J Haematol*, (2002) 119(2):400-407.
Park et al., Monensin-mediated growth inhibition in NCI-H929 myeloma cells via cycle arrest apoptosis, *Int J Oncol*, (2003) 23(1):197-204.
Poljiak et al., Production and structure of diabodies, *Structure* (1994) 2:1121-1123.
Roque et al., Antibodies and genetically engineered related molecules: production and purification, *Biotechnol Prog*, (2004) 20:639-654.
Rothman R J et al., "Antibody-dependent cytotoxicity mediated by natural killer cells is enhanced by castanospermine-induced alterations of IgG glycosylation", Molecular Immunology, vol. 26, No. 12, Dec. 1, 1989, pp. 1113-1123.
Stettler et al., New disposable tubes for rapid and precise biomass assessment for suspension cultures of mammalian cells, *Biotechnol Bioeng* (2006) 20:95(6):1228-1233.
Tenaglia et al., Amphotericin-B and monensin potentiation of murine erythropoiesis in vitro : a possible role for sodium ions, *Exp Hematol* (1985) 13(6):512-519.
Urlaub et al., Isolation of Chinese hamster cell mutants deficient in dihydrofolate reductase activity, *Proc Natl Acad Sci USA*, (1980) 77(7):4216-4220.
Ward et al., Binding activities of a repertoire of single immunoglobulin variable domains secreted from *Escherichia coli*, Nature (1989) 341:544-546.
Wong et al., Impact of dynamic online fed-batch strategies on metabolism, productivity and N-glycosylation quality in CHO cell cultures, *Biotechnol Bioeng* (2005) 89(2):164-177.
Wood et al., High levels of synthesis of immunoglobulins in Chinese hamster ovary cells, *J Immul*, (1990) 145:3011-3016.
Wrighi et al., Effect of glycosylation on antibody function: implications for genetic engineering, *Trends in Biotechnol* (1997) 15(1):26-32.
Yu et al., Production, characterization and pharmacokinetic properties of antibodies with N-linked Mannose-5 glycans, mAbs (2012) 4(4):475-487.
Zhou, Q et al., "Development of a Simple and Rapid Method for Producing Non-Fucosylated Oligomannose Containing Antibodies With Increased Effector Function", Biotechnology and Bioengineering 2007, vol. 99, No. 3, p. 652-665.

USE OF MONENSIN TO REGULATE GLYCOSYLATION OF RECOMBINANT PROTEINS

CROSS REFERENCE TO RELATED APPLICATIONS

This application is a continuation of U.S. application Ser. No. 15/033,559, now U.S. Pat. No. 11,130,980, filed Apr. 29, 2016, which is a National Stage application under 35 U.S.C. § 371 of International Application No. PCT/US2014/063211, having an international filing date of Oct. 30, 2014, which claims the benefit of U.S. Provisional Patent Application No. 61/898,310, filed Oct. 31, 2013, all of which are incorporated herein by reference in their entirety.

FIELD OF THE INVENTION

The present invention relates generally to compounds and processes for modulating one or more properties of a recombinant protein produced by cell culture, including mammalian cell cultures such as CHO cell cultures.

BACKGROUND OF THE INVENTION

Glycosylation is a ubiquitous post-translational modification in mammalian cells; both normal human immunoglobulins and therapeutic monoclonal antibodies (mAbs) produced in Chinese hamster ovary (CHO) cells are glycoproteins. Although the glycoforms of a protein expressed by CHO host cells are largely determined during cell line generation and clone selection, the presence and/or degree of high mannose glycoform content can also be affected by cell culture conditions (Pacis et al., (2011) *Biotechnol Bioeng* 108, 2348-2358).

Both pharmacokinetic properties and effector functions of therapeutic mAbs can be affected by glycosylation of the constant region. Terminal sugars such as fucose and galactose may affect antibody-dependent cellular cytoxicity (ADCC) and complement-dependent cytoxicity (CDC; Wright, A. and S. L. Morrison, *Trends Biotechnol* (1997) 15:26-32). High mannose glycans may increase serum clearance of certain mAbs thus potentially affecting efficacy (Goetze, et al., (2011) *Glycobiology* 21:949-59). Alternatively, high mannose glycoforms can increase the affinity of antibodies for Fc gamma III receptor thus increasing ADCC activity of certain antibodies (Yu, et al. (2012) *MAbs* 4:475-87). Thus for each recombinant mAb a certain glycosylation profile that best supports the therapeutic potential of the mAb needs to be maintained.

Methods for manipulating high mannose glycoform content of a protein in cell culture include changes in media compositions, osmolality, pH, temperature, etc (Yu, et al., supra, Pacis et al., supra, Chee Furng Wong et al. (2005) *Biotechnol Bioeng* 89:164-177; Ahn, et al. (2008) *Biotechnol Bioeng* 101:1234-44). The effectiveness of these methods is specific to cell lines, molecule types and media environment and is typically obtained by trial and error. Additionally, these methods tend to also alter antibody productivity, cell culture behavior and other antibody quality attributes.

Monensin is a sodium-hydrogen inophore capable of integrating into biological membranes and thus disturbing sodium-hydrogen gradients across those membranes. It is widely used as an antibiotic in the cattle and fowl industry and as a tool for studying intracellular vesicular trafficking in cultured eukaryotic cells. Addition of monensin has been reported to inhibit secretion of many different proteins from various cell types (Fukao, H., et al. (1989) 14:673-84; Kuhn, L. J., et al (1986). *J Biol Chem* 261:3816-25). Monensin also inhibits glycan processing by neutralizing the pH of the Golgi thus affecting the function of various glycosylation enzymes (Kubo, R. T. and M. L. Pigeon, (1983) *Mol Immunol* 20:345-8).

It has been observed that the addition of monensin leads to an increase in high mannose glycoforms on a variety of different proteins expressed in various cell systems (Machamer, C. E. and P. Cresswell (1984) *Proc Natl Acad Sci USA* 81:1287-91; Kousoulas, K. G., et al. (1983) *Intervirology* 20: 56-60; Chatterjee, S., et al., (1982) J Virol 44:1003-12). However, in most of the published reports short term application of monensin is used to study its effects on glycan processing; prolonged administration of monensin at micromolar concentrations is toxic to the cells. Also, no studies have evaluated the utility of monensin to modulate the high mannose profile of therapeutic antibodies produced by CHO production cell lines.

There still exists a need to identify a universal mechanism which can increase high mannose glycoforms (particularly Mannose 5), on mAbs without compromising CHO production culture performance and antibody yield. Such a method would benefit the process development of therapeutic proteins. The invention provides a method that regulates high mannose glycoform content by contacting cells expressing a therapeutic protein with monensin.

SUMMARY OF THE INVENTION

The present invention provides a method for regulating the high mannose glycoform content of a recombinant protein during a mammalian cell culture process comprising establishing a mammalian cell culture in a bioreactor, and contacting the cell culture with monensin. Optionally, the invention further comprises a step of harvesting the recombinant protein produced by the cell culture. In a further embodiment the recombinant protein produced by the cell culture is purified and formulated in a pharmaceutically acceptable formulation.

In a further embodiment the high mannose glycoform content of a recombinant protein is increased compared to that produced by a culture where the cells are not contacted with monensin. In one embodiment the high mannose glycan species is Mannose 5 (Man5). In another embodiment, the high mannose glycan species is Mannose 6 (Man6), Mannose 7 (Man7), Mannose 8 (including Mannose 8a and 8b; Man8a and 8b, or Mannose 9 (Man9). In a further embodiment the high mannose glycan species comprise a mixture of Man5, Man6, Man7, Man8a, Man8b, and/or Man9.

The invention provides a further embodiment in which the high mannose glycoform content of a recombinant protein is less than 10%. In another embodiment, the high mannose glycoform content of a recombinant protein is greater than or equal to 10%. In a further embodiment, the high mannose glycoform content of a recombinant protein produced by a cell culture that is contacted with monensin is greater than that produced by a cell culture that is not contacted with monensin by one percentage point, two percentage points, three percentage points, four percentage points or 5 percentage points. In yet another embodiment, high mannose glycoform content of a recombinant protein produced by a cell culture that is contacted with monensin is greater than that produced by a cell culture that is not contacted with monensin by a 6, 7, 8, 9, or 10 percentage points. In further embodiments high mannose glycoform content of a recombinant protein produced by a cell culture that is contacted with monensin is greater than that produced by a cell culture that is not contacted with monensin by a 12, 15, 17, 20, 22, 25, 27, 30, 32, 35, 37 or 40 percentage points. In yet another embodiment, the high mannose glycoform content of a recombinant protein produced by a cell culture that is contacted with monensin is greater than that produced by a cell culture that is not contacted with monensin by 50 percentage points or more (i.e., 60, 70, 80, 90 or 100 percentage points).

In one embodiment, monensin is added to the cell culture in a single bolus dose to achieve a final concentration. In one embodiment, the final concentration of monensin in the medium is 0.1 nM-1000 nM; in another embodiment, the concentration is 10 nM-800 nM; in another the final concentration is 25 nM-750 nM; in yet another embodiment, the final concentration is 50 nM-500 nM. Further aspects of the invention include a method for regulating the high mannose glycoform content of a recombinant protein during a mammalian cell culture process by including monensin in the cell culture medium at a final concentration of 50 nM, 100 nM, 250 nM; 500 nM; or of 750 nM.

One embodiment of the invention provides a method for regulating the high mannose glycoform content of a recombinant protein during a mammalian cell culture process by feeding the cells with a medium containing monensin, or to which monensin is added, continuously for between one and three days. In one embodiment, the monensin is present in the cell culture (by virtue of being added to the medium or being added to the culture along with medium) for approximately one day (20-28 hours); for approximately two days (40-56 hours) or approximately three days (60-84 hours). In a further embodiment, the monensin is present in the cell culture (by virtue of being added to the medium or being added to the culture along with medium) for four days, five days, six days, seven days, eight days, nine days 10 days or longer. For additional embodiments, the monensin is present in the cell culture for the entire duration of the culture process. In these embodiment, the monensin may be present at a set, selected concentration, or it may be present in increasing concentration, or in an initial concentration that is increased to a higher concentration before being decreased again to the original concentration or another, lower concentration, as described herein.

A further embodiment of the invention provides a method for regulating the high mannose glycoform content of a recombinant protein during a mammalian cell culture process by contacting the cells with a medium containing monensin, and simultaneously or sequentially adding monensin separately to the culture. Additional embodiments include the use of monensin in a fed-batch culture and the use of monensin in a perfusion culture. In one embodiment, the culture is perfused using alternating tangential flow (ATF). In one embodiment, the monensin is present in the cell culture by virtue of being added to the culture in the medium at a selected concentration for a selected period of time, as herein described, and the concentration of monensin is increased, at a selected point of time and for a selected period of time, by the addition of monensin to the culture separately from, but optionally along with, the feed medium or the perfusion medium.

The invention further provides for the addition of monensin to the cell culture between three and 15 days after the culture is established. In one embodiment, monensin is added to the cell culture at day 3, at day 4, at day 5; at day 6; at day 7; at day 8; at day 9; at day 10; at day 11; or at day 12 after the culture is established. The monensin is maintained at a concentration as previously described (in one embodiment, at a final concentration of 25 nM, 50 nM, 100 nM, 250 nM, of 500 nM or of 750 nM) for a period of time between one and seven days, and may be added by any of the herein mentioned methods (i.e., inclusion in feed medium, addition separately from feed medium, etc.).

A further embodiment of the invention provides for the addition of monensin to the cell culture between one and 15 days before the cell culture is harvested. In yet another embodiment, the monensin is present for the entire duration of the cell culture, from day 0 through harvest. In one embodiment, monensin is added to the cell culture one day before harvest; two days, three days; four days; five days; six days; seven days; eight days; nine days; or ten days before harvest. The monensin is maintained at a concentration as previously described (in one embodiment, at a final concentration of 25 nM, 50 nM, 100 nM, 250 nM, of 500 nM or of 750 nM; in another embodiment, at one of the aforementioned ranges) for a period of time between one and three days. In a further embodiment, the amount of monensin is increased overtime, to a steady state or to a concentration from which it is then decreased, as described herein.

In yet another aspect of the invention, the addition of monensin to the cell culture begins between one and 15 days after the culture is established, or between three and 15 days after the culture is established, and optionally continues until the cell culture is harvested. In one embodiment, monensin is added to the cell culture one day after the culture is established; two days, three days; four days; five days; six days; seven days; eight days; nine days; or ten days after the culture is established. In a further embodiment, monensin is added to the cell culture 11 days, 12 days; 13 days; 14 days; 15 days; 16 days; 17 days; 18 days; 19 days; 20 days; 21 days or 22 days after establishment of the culture. As previously described, in one embodiment, monensin is present for the entire duration of the cell culture, from day 0 through harvest. In another embodiment, the monensin is maintained at a concentration as described above (in one embodiment, at a final concentration of 25 nM, 50 nM, 100 nM, 250 nM, of 500 nM or of 750 nM; in another embodiment, at one of the aforementioned ranges) for a period of time between one and three days. In a further embodiment, the amount of monensin is increased over time, to a steady state or to a concentration from which it is then decreased, as described herein.

In one embodiment of the invention, monensin is added to the cell culture to achieve a constant concentration; in another embodiment, the concentration of monensin is varied. For one embodiment, the concentration of monensin in the cell culture may be held at 25 nM for from three to five days, then increased (or ramped up) to 50 nM for from one day through the duration of the culture. In another embodiment, the concentration of monensin in the cell culture may be held at 25 nM for from three to five days, then increased to 50 nM for three to five days, then tapered again to 25 nM for the duration of the culture. Additional embodiments comprise shorter or longer time periods during which the levels of monensin are increased, held steady, and optionally decreased, for example, increased over a period of from one to two days, held steady for a period of from one to two days, and optionally decreased for a period of from one to two days.

The invention further includes varying the concentration of monensin from between 25 nM and 100 nM to between 100 nM and 500 nM, and maintaining the second, higher concentration of monensin for a period of from one day through the duration of the culture. In another embodiment, the method optionally comprises a tapering step that reduces the concentration of monensin to between 25 nM and 100 nM (for a period of from one day through the duration of the culture). The duration of each stage can be varied, as described, holding the monensin at a selected level for from three to five days at each stage. Longer time periods may also be employed, as may other variations such as gradually increasing the amount of monensin over a time period and holding the monensin concentration, or decreasing it gradually.

In one embodiment, the monensin is included in the medium, which can be a feed medium or a perfusion medium, at a selected final concentration (i.e., 25 nM, 50 nM, 100 nM, 250 nM, of 500 nM or of 750 nM); in another embodiment, the monensin is added to the cell culture along with the medium, in yet another embodiment the monensin is added separately from the medium. The monensin is added to the culture at a rate sufficient to achieve and/or maintain a desired final concentration in the culture. In one embodiment, the monensin is added at a rate of $1/40$-$1/60$ of the rate at which medium is added to the culture, for example by perfusion; in another embodiment, the monensin is added at a rate of $1/50$ of the rate. In further embodiments, the rate is varied to achieve a desired concentration using calculations that are known in the art. The monensin can be added at a rate that is from $1/10$ of that of the culture medium to $1/100$ of that of the culture medium.

In combination with any of the embodiments of the invention described herein, antifoam may also added into the culture vessel as needed. Alternatively or additionally, 1M Sodium Carbonate or another suitable base is used to maintain pH at the desired setpoint.

As described herein, in one aspect of the invention the cell culture may be maintained by perfusion. In one embodiment perfusion begins on or about day 1 to on or about day 9 of the cell culture. In a related embodiment perfusion begins on or about day 3 to on or about day 7 of the cell culture. In one embodiment perfusion begins when the cells have reached a production phase. In further embodiments of the invention, perfusion is accomplished by alternating tangential flow. In a related embodiment the perfusion is accomplished by alternating tangential flow using an ultrafilter or a microfilter.

A further embodiment of the invention provides continuous perfusion; in yet a further embodiment the rate of perfusion is constant. One embodiment of the invention provides perfusion performed at a rate of less than or equal to 1.0 working volumes per day. In a related embodiment perfusion is performed at a rate that increases during the production phase from 0.25 working volume per day to 1.0 working volume per day during the cell culture. In another related embodiment perfusion is performed at a rate that reaches 1.0 working volume per day on day 9 to day 11 of the cell culture. In another related embodiment perfusion is performed at a rate that reaches 1.0 working volume per day on day 10 of the cell culture.

In one embodiment the cell culture receives bolus cell culture media feeds prior to days 3-7 of the culture.

In yet another aspect of the invention, the cell culture is maintained by fed batch. In one embodiment of a fed batch culture, the culture is fed three times during production. In a further embodiment, the culture is fed on a day between day two and four, on a day between day 5 and 7, and on a day between day 8 and 10. Another embodiment provides a fed batch method in which the culture is fed four times during production. In a still further embodiment, the culture is fed on a day between day two and four, on a day between day 5 and 6, on a day between day 7 and 8, and on a day between day 8 and 10 or later.

In one embodiment of the invention, monensin is added to a fed batch culture along with the feed medium. Thus, monensin may be added three or four times during the production process, at the times set forth previously. The monensin may be added to the medium (i.e., production medium) at a concentration designed to achieve a particular concentration in the culture, or the monensin may be added to the culture separately from, but along with, the feed medium. In another embodiment, the monensin is added directly to he culture on a day or days during which the culture is not being fed (i.e., no additional feed medium is added). The concentration of the monensin and the amount of time it is present in the culture is selected according to the aforementioned parameters.

According to one embodiment of the invention, the mammalian cell culture is established by inoculating the bioreactor with at least $0.5 \times 10^6$ to $3.0 \times 10^6$ cells/mL in a serum-free culture media. In an alternate or further embodiment the mammalian cell culture is established by inoculating the bioreactor with at least $0.5 \times 10^6$ to $1.5 \times 10^6$ cells/mL in a serum-free culture media.

The invention may further comprise a temperature shift during the culture. In one embodiment the temperature shift is from 36° C. to 31° C. In one embodiment the invention further comprises a temperature shift from 36° C. to 33° C. In a related embodiment the temperature shift occurs at the transition between the growth phase and production phase. In a related embodiment the temperature shift occurs during the production phase.

In another embodiment the invention further comprises inducing cell growth-arrest by L-asparagine starvation followed by perfusion with a serum-free perfusion media having an L-asparagine concentration of 5 mM or less. In another embodiment the invention further comprises inducing cell growth-arrest by perfusion with a serum-free perfusion media having an L-asparagine concentration of 5 mM or less. In a related embodiment the concentration of L-asparagine in the serum-free perfusion media is less than or equal to 5 mM. In a related embodiment the concentration of L-asparagine in the serum-free perfusion media is less than or equal to 4.0 mM. In a related embodiment the concentration of L-asparagine in the serum-free perfusion media is less than or equal to 3.0 mM. In a related embodiment the concentration of L-asparagine in the serum-free perfusion media is less than or equal to 2.0 mM. In a related embodiment the concentration of L-asparagine in the serum-free perfusion media is less than or equal to 1.0 mM. In a related embodiment the concentration of L-asparagine in the serum-free perfusion media is 0 mM. In a related embodiment the L-asparagine concentration of the cell culture media is monitored prior to and during L-asparagine starvation.

In yet another embodiment the invention comprises that the packed cell volume during a production phase is less than or equal to 35%. In a related embodiment the packed cell volume is less than or equal to 35%. In a related embodiment the packed cell volume is less than or equal to 30%.

In a related embodiment the viable cell density of the mammalian cell culture at a packed cell volume less than or equal to 35% is $10 \times 10^6$ viable cells/ml to $80 \times 10^6$ viable cells/ml. In another embodiment the viable cell density of the mammalian cell culture is $20 \times 10^6$ viable cells/ml to $30 \times 10^6$ viable cells/ml.

In yet another embodiment the bioreactor has a capacity of at least 500 L. In yet another embodiment the bioreactor has a capacity of at least 500 L to 2000 L. In yet another embodiment the bioreactor has a capacity of at least 1000 L to 2000 L.

In yet another embodiment the mammalian cells are Chinese Hamster Ovary (CHO) cells. In yet another embodiment the recombinant protein is selected from the group consisting of a human antibody, a humanized antibody, a chimeric antibody, a recombinant fusion protein, or a cytokine.

BRIEF DESCRIPTION OF THE DRAWINGS

FIG. 2 presents the results of viability analysis. In FIG. 3, the packed cell volume of the monensin and control tanks, monitored on a daily basis throughout the course of the experiment, is shown. Daily spent medium samples were also submitted for titer analysis. Packed cell volume and titer values were used to calculate packed cell-adjusted titers, which are shown in FIG. 4.

FIG. 7 depicts the same analysis for Ra reactor, and FIG. 8 for the Rb reactor.

DETAILED DESCRIPTION OF THE INVENTION

Figure 1:
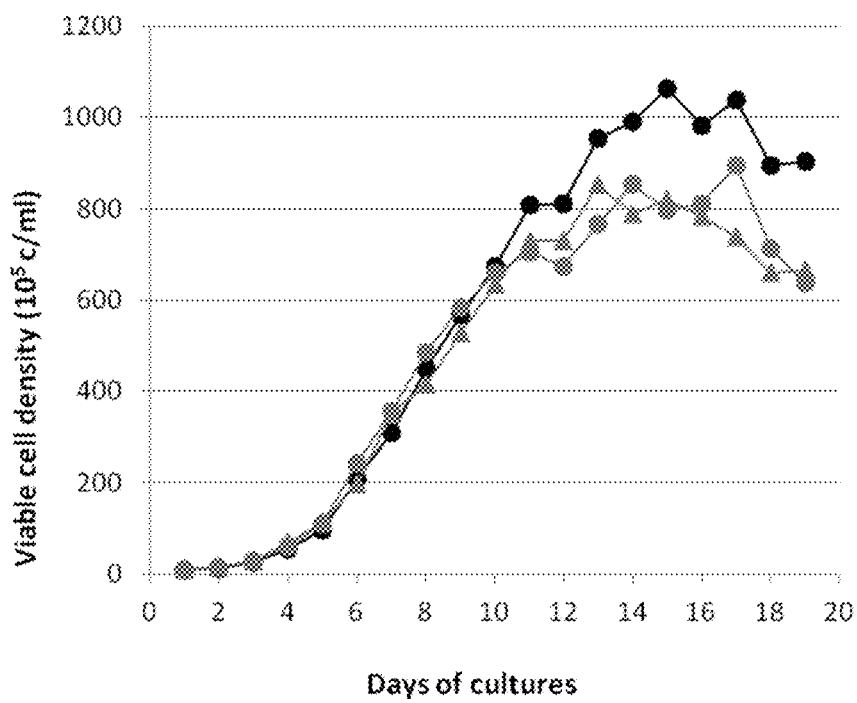
FIGS. 1 through 4 present the results obtained when evaluating the effect of monensin on cell culture performance in bioreactors using alternating tangential (ATF). Monensin concentration in ATF reactors Ra (gray triangle) and Rb (gray circles) was held at 500 nM over the course of ~22 hors starting on day 8 and ending on day 9. Cells in the control reactor (black circles) were grown in the absence of monensin. Viable cell density is illustrated in FIG. 1.
Figure 2:
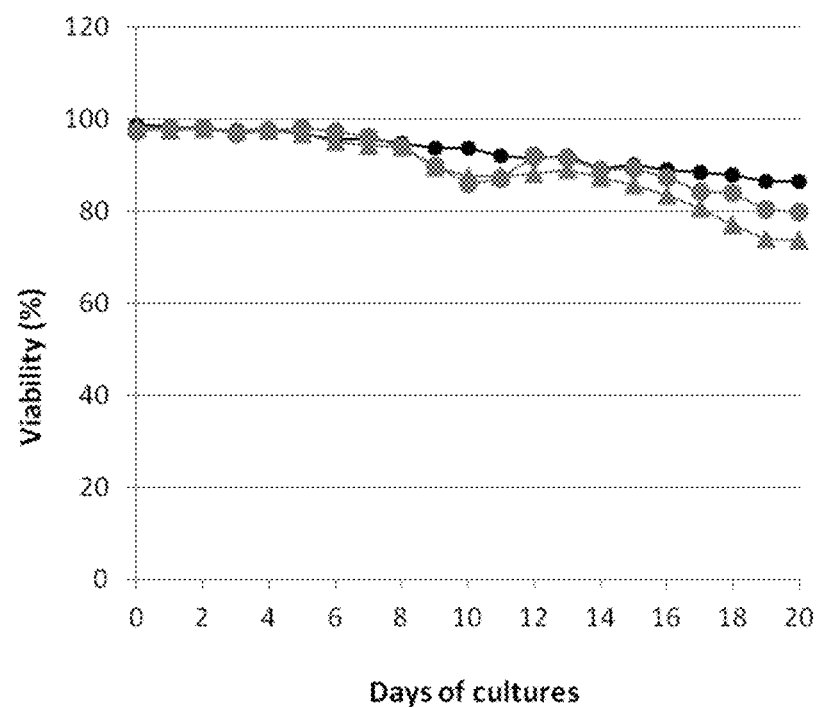

While the terminology used in this application is standard within the art, definitions of certain terms are provided herein to assure clarity and definiteness in the meaning of the claims. Units, prefixes, and symbols may be denoted in their SI (International System of Units) accepted form. Numeric ranges recited herein are inclusive of the numbers defining the range and include and are supportive of each integer within the defined range. The methods and techniques described herein are generally performed according to conventional methods well known in the art and as described in various general and more specific references that are cited and discussed throughout the present specification unless otherwise indicated. See, e.g., Sambrook et al. Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990).

The disclosed methods are applicable to adherent culture or suspension cultures grown in stirred tank reactors (including traditional batch and fed-batch cell cultures, which may but need not comprise a spin filter), perfusion systems (including alternating tangential flow ("ATF") cultures, acoustic perfusion systems, depth filter perfusion systems, and other systems), hollow fiber bioreactors (HFB, which in some cases may be employed in perfusion processes) as well as various other cell culture methods (see, e.g., Tao et al., (2003) *Biotechnol. Bioeng.* 82:751-65; Kuystermans & Al-Rubeai, (2011) "Bioreactor Systems for Producing Antibody from Mammalian Cells" in *Antibody Expression and Production*, Cell Engineering 7:25-52, Al-Rubeai (ed) Springer; Catapano et al., (2009) "Bioreactor Design and Scale-Up" in *Cell and Tissue Reaction Engineering: Principles and Practice*, Eibl et al. (eds) Springer-Verlag, incorporated herein by reference in their entireties).

All documents, or portions of documents, cited in this application, including but not limited to patents, patent applications, articles, books, and treatises, are hereby expressly incorporated by reference. What is described in an embodiment of the invention can be combined with other embodiments of the invention.

Definitions

As used herein, the terms "a" and "an" mean one or more unless specifically indicated otherwise. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art.

The instant disclosure provides methods of modulating the properties of cell cultures expressing a "protein of interest;" "protein of interest" includes naturally occurring proteins, recombinant proteins, and engineered proteins (e.g., proteins that do not occur in nature and which have been designed and/or created by humans). A protein of interest can, but need not be, a protein that is known or suspected to be therapeutically relevant. Particular examples of a protein of interest include antigen binding proteins (as described and defined herein), peptibodies (i.e., a molecule comprising peptide(s) fused either directly or indirectly to other molecules such as an Fc domain of an antibody, where the peptide moiety specifically binds to a desired target; the peptide(s) may be fused to either an Fc region or inserted into an Fc-Loop, or a modified Fc molecule, for example as described in U.S. Patent Application Publication No. US2006/0140934 incorporated herein by reference in its entirety), fusion proteins (e.g., Fc fusion proteins, wherein a Fc fragment is fused to a protein or peptide), cytokines, growth factors, hormones and other naturally occurring secreted proteins, as well as mutant forms of naturally occurring proteins.

The term "antigen binding protein" is used in its broadest sense and means a protein comprising a portion that binds to an antigen or target and, optionally, a scaffold or framework portion that allows the antigen binding portion to adopt a conformation that promotes binding of the antigen binding protein to the antigen. Examples of antigen binding proteins include a human antibody, a humanized antibody; a chimeric antibody; a recombinant antibody; a single chain antibody; a diabody; a triabody; a tetrabody; a Fab fragment; a F(ab')$_2$ fragment; an IgD antibody; an IgE antibody; an IgM antibody; an IgG1 antibody; an IgG2 antibody; an IgG3 antibody; or an IgG4 antibody, and fragments thereof. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, e.g., Korndorfer et al., 2003, *Proteins: Structure, Function, and Bioinformatics*, 53(1): 121-129 (2003); Roque et al., *Biotechnol. Prog.* 20:639-654 (2004). In addition, peptide antibody mimetics ("PAMs") can be used, as well as scaffolds based on antibody mimetics utilizing fibronectin components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively.

Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain can be done in accordance with the definitions of Kabat et al. in Sequences of Proteins of Immunological Interest, 5$^{th}$ Ed., US Dept. of Health and Human Services, PHS, NIH, NIH Publication no. 91-3242, (1991). As desired, the CDRs can also be redefined according an alternative nomenclature scheme, such as that of Chothia (see Chothia & Lesk, (1987) *J. Mol. Biol.* 196:901-917; Chothia et al., (1989) *Nature* 342:878-883 or Honegger & Pluckthun, (2001) *J. Mol. Biol.* 309:657-670).

In the context of the instant disclosure an antigen binding protein is said to "specifically bind" or "selectively bind" its target antigen when the dissociation constant ($K_D$) is $\leq 10^{-8}$ M. The antibody specifically binds antigen with "high affinity" when the $K_D$ is $\leq 5\times 10^{-9}$ M, and with "very high affinity" when the $K_D$ is $\leq 5\times 10^{-8}$ M.

The term "antibody" includes reference to both glycosylated and non-glycosylated immunoglobulins of any isotype or subclass or to an antigen-binding region thereof that competes with the intact antibody for specific binding, unless otherwise specified. Additionally, the term "antibody" refers to an intact immunoglobulin or to an antigen binding portion thereof that competes with the intact antibody for specific binding, unless otherwise specified. Antigen binding portions can be produced by recombinant DNA techniques or by enzymatic or chemical cleavage of intact antibodies and can form an element of a protein of interest. Antigen binding portions include, inter alia, Fab, Fab', F(ab')$_2$, Fv, domain antibodies (dAbs), fragments including complementarity determining regions (CDRs), single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_H1$ domains; a F(ab')$_2$ fragment is a bivalent fragment having two Fab fragments linked by a disulfide bridge at the hinge region; a Fd fragment has the $V_H$ and $C_H1$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634, 6,696,245, U.S. App. Pub. Nos. 05/0202512, 04/0202995, 04/0038291, 04/0009507, 03/0039958, Ward et al., (1989) *Nature* 341: 544-546).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., *Science* 242:423-26 (1988) and Huston et al., (1988) *Proc. Natl. Acad. Sci. USA* 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., (1993) *Proc. Natl. Acad. Sci. USA* 90:6444-48; and Poljak et al., (1994) *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

One or more CDRs can be incorporated into a molecule either covalently or noncovalently to make it an antigen binding protein. An antigen binding protein can incorporate the CDR(s) as part of a larger polypeptide chain, can covalently link the CDR(s) to another polypeptide chain, or can incorporate the CDR(s) noncovalently. The CDRs permit the antigen binding protein to specifically bind to a particular antigen of interest.

An antigen binding protein can have one or more binding sites. If there is more than one binding site, the binding sites can be identical to one another or can be different. For example, a naturally occurring human immunoglobulin typically has two identical binding sites, while a "bispecific" or "bifunctional" antibody has two different binding sites.

For purposes of clarity, and as described herein, it is noted that an antigen binding protein can, but need not, be of human origin (e.g., a human antibody), and in some cases will comprise a non-human protein, for example a rat or murine protein, and in other cases an antigen binding protein can comprise a hybrid of human and non-human proteins (e.g., a humanized antibody).

A protein of interest can comprise a human antibody. The term "human antibody" includes all antibodies that have one or more variable and constant regions derived from human immunoglobulin sequences. In one embodiment, all of the variable and constant domains are derived from human immunoglobulin sequences (a fully human antibody). Such antibodies can be prepared in a variety of ways, including through the immunization with an antigen of interest of a mouse that is genetically modified to express antibodies derived from human heavy and/or light chain-encoding genes, such as a mouse derived from a Xenomouse®, UltiMab™, or Velocimmune® system. Phage-based approaches can also be employed.

Alternatively, a protein of interest can comprise a humanized antibody. A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. Examples of how to make humanized antibodies can be found in U.S. Pat. Nos. 6,054,297, 5,886,152 and 5,877,293.

An "Fc" region, as the term is used herein, comprises two heavy chain fragments comprising the $C_H2$ and $C_H3$ domains of an antibody. The two heavy chain fragments are held together by two or more disulfide bonds and by hydrophobic interactions of the $C_H3$ domains. Proteins of interest comprising an Fc region, including antigen binding proteins and Fc fusion proteins, form another aspect of the instant disclosure.

A "hemibody" is an immunologically functional immunoglobulin construct comprising a complete heavy chain, a complete light chain and a second heavy chain Fc region paired with the Fc region of the complete heavy chain. A linker can, but need not, be employed to join the heavy chain Fc region and the second heavy chain Fc region. In particular embodiments a hemibody is a monovalent form of an antigen binding protein disclosed herein. In other embodiments, pairs of charged residues can be employed to associate one Fc region with the second Fc region. A hemibody can be a protein of interest in the context of the instant disclosure.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present. A cell culture can comprise one or more host cells.

The term "hybridoma" means a cell or progeny of a cell resulting from fusion of an immortalized cell and an antibody-producing cell. The resulting hybridoma is an immortalized cell that produces antibodies. The individual cells used to create the hybridoma can be from any mammalian source, including, but not limited to, hamster, rat, pig, rabbit, sheep, goat, and human. The term also encompasses trioma cell lines, which result when progeny of heterohybrid myeloma fusions, which are the product of a fusion between human cells and a murine myeloma cell line, are subsequently fused with a plasma cell. The term is meant to include any immortalized hybrid cell line that produces antibodies such as, for example, quadromas (see, e.g., Milstein et al., (1983)*Nature*, 537:3053).

The terms "culture" and "cell culture" are used interchangeably and refer to a cell population that is maintained in a medium under conditions suitable to survival and/or growth of the cell population. As will be clear to those of ordinary skill in the art, these terms also refer to the combination comprising the cell population and the medium in which the population is suspended.

The terms "polypeptide" and "protein" (e.g., as used in the context of a protein of interest or a polypeptide of interest) are used interchangeably herein to refer to a polymer of amino acid residues. The terms also apply to amino acid polymers in which one or more amino acid residues is an analog or mimetic of a corresponding naturally occurring amino acid, as well as to naturally occurring amino acid polymers. The terms can also encompass amino acid polymers that have been modified, e.g., by the addition of carbohydrate residues to form glycoproteins, or phosphorylated. Polypeptides and proteins can be produced by a naturally-occurring and non-recombinant cell, or polypeptides and proteins can be produced by a genetically-engineered or recombinant cell. Polypeptides and proteins can comprise molecules having the amino acid sequence of a native protein, or molecules having deletions from, additions to, and/or substitutions of one or more amino acids of the native sequence.

The terms "polypeptide" and "protein" encompass molecules comprising only naturally occurring amino acids, as well as molecules that comprise non-naturally occurring amino acids. Examples of non-naturally occurring amino acids (which can be substituted for any naturally-occurring amino acid found in any sequence disclosed herein, as desired) include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

A non-limiting list of examples of non-naturally occurring amino acids that can be inserted into a protein or polypeptide sequence or substituted for a wild-type residue in a protein or polypeptide sequence include β-amino acids, homoamino acids, cyclic amino acids and amino acids with derivatized side chains. Examples include (in the L-form or D-form;

abbreviated as in parentheses): citrulline (Cit), homocitrulline (hCit), Nα-methylcitrulline (NMeCit), Nα-methylhomocitrulline (Nα-MeHoCit), ornithine (Orn), Nα-Methylornithine (Nα-MeOrn or NMeOm), sarcosine (Sar), homolysine (hLys or hK), homoarginine (hArg orhR), homoglutamine (hQ), Nα-methylarginine (NMeR), Nα-methylleucine (Na-MeL or NMeL), N-methylhomolysine (NMeHoK), Nα-methylglutamine (NMeQ), norleucine (Nle), norvaline (Nva), 1,2,3,4-tetrahydroisoquinoline (Tic), Octahydroindole-2-carboxylic acid (Oic), 3-(1-naphthyl) alanine (1-Nal), 3-(2-naphthyl)alanine (2-Nal), 1,2,3,4-tetrahydroisoquinoline (Tic), 2-indanylglycine (IgI), para-iodophenylalanine (pI-Phe), para-aminophenylalanine (4 AmP or 4-Amino-Phe), 4-guanidino phenylalanine (Guf), glycyllysine (abbreviated "K(Nε-glycyl)" or "K(glycyl)" or "K(gly)"), nitrophenylalanine (nitrophe), aminophenylalanine (aminophe or Amino-Phe), benzylphenylalanine (benzylphe), γ-carboxyglutamic acid (γ-carboxyglu), hydroxyproline (hydroxypro), p-carboxyl-phenylalanine (Cpa), α-aminoadipic acid (Aad), Nα-methyl valine (NMeVal), N-α-methyl leucine (NMeLeu), Nα-methylnorleucine (NMeNle), cyclopentylglycine (Cpg), cyclohexylglycine (Chg), acetylarginine (acetylarg), α, β-diaminopropionoic acid (Dpr), α, γ-diaminobutyric acid (Dab), diaminopropionic acid (Dap), cyclohexylalanine (Cha), 4-methyl-phenyl-alanine (MePhe), β, β-diphenyl-alanine (BiPhA), aminobutyric acid (Abu), 4-phenyl-phenylalanine (or biphenylalanine; 4Bip), α-amino-isobutyric acid (Aib), beta-alanine, beta-aminopropionic acid, piperidinic acid, aminocaprioic acid, aminoheptanoic acid, aminopimelic acid, desmosine, diaminopimelic acid, N-ethylglycine, N-ethylaspargine, hydroxylysine, allo-hydroxylysine, isodesmosine, allo-isoleucine, N-methylglycine, N-methylisoleucine, N-methylvaline, 4-hydroxyproline (Hyp), γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-methylarginine, 4-Amino-O-Phthalic Acid (4APA), and other similar amino acids, and derivatized forms of any of those specifically listed.

By "cell culture" or "culture" is meant the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992). Mammalian cells may be cultured in suspension or while attached to a solid substrate. Fluidized bed bioreactors, hollow fiber bioreactors, roller bottles, shake flasks, or stirred tank bioreactors, with or without microcarriers, can be used. In one embodiment 500 L to 2000 L bioreactors are used. In one embodiment, 1000 L to 2000 L bioreactors are used.

The term "cell culturing medium" (also called "culture medium," "cell culture media," "tissue culture media,") refers to any nutrient solution used for growing cells, e.g., animal or mammalian cells, and which generally provides at least one or more components from the following: an energy source (usually in the form of a carbohydrate such as glucose); one or more of all essential amino acids, and generally the twenty basic amino acids, plus cysteine; vitamins and/or other organic compounds typically required at low concentrations; lipids or free fatty acids; and trace elements, e.g., inorganic compounds or naturally occurring elements that are typically required at very low concentrations, usually in the micromolar range.

The nutrient solution may optionally be supplemented with additional optional components to optimize growth of cells, such as hormones and other growth factors, e.g., insulin, transferrin, epidermal growth factor, serum, and the like; salts, e.g., calcium, magnesium and phosphate, and buffers, e.g., HEPES; nucleosides and bases, e.g., adenosine, thymidine, hypoxanthine; and protein and tissue hydrolysates, e.g., hydrolyzed animal or plant protein (peptone or peptone mixtures, which can be obtained from animal byproducts, purified gelatin or plant material); antibiotics, e.g., gentamycin; cell protectants or surfactants such as Pluronic®F68 (also referred to as Lutrol® F68 and Kolliphor® P188; nonionic triblock copolymers composed of a central hydrophobic chain of polyoxypropylene (poly(propylene oxide)) flanked by two hydrophilic chains of polyoxyethylene (poly(ethylene oxide)); polyamines, e.g., putrescine, spermidine and spermine (see e.g., WIPO Publication No. WO 2008/154014) and pyruvate (see e.g. U.S. Pat. No. 8,053,238) depending on the requirements of the cells to be cultured and/or the desired cell culture parameters.

Cell culture media include those that are typically employed in and/or are known for use with any cell culture process, such as, but not limited to, batch, extended batch, fed-batch and/or perfusion or continuous culturing of cells.

A "base" (or batch) cell culture medium refers to a cell culture medium that is typically used to initiate a cell culture and is sufficiently complete to support the cell culture.

A "growth" cell culture medium refers to a cell culture medium that is typically used in cell cultures during a period of exponential growth, a "growth phase", and is sufficiently complete to support the cell culture during this phase. A growth cell culture medium may also contain selection agents that confer resistance or survival to selectable markers incorporated into the host cell line. Such selection agents include, but are not limited to, geneticin (G4118), neomycin, hygromycin B, puromycin, zeocin, methionine sulfoximine, methotrexate, glutamine-free cell culture medium, cell culture medium lacking glycine, hypoxanthine and thymidine, or thymidine alone.

A "production" cell culture medium refers to a cell culture medium that is typically used in cell cultures during the transition when exponential growth is ending and protein production takes over, "transition" and/or "product" phases, and is sufficiently complete to maintain a desired cell density, viability and/or product titer during this phase.

A "perfusion" cell culture medium refers to a cell culture medium that is typically used in cell cultures that are maintained by perfusion or continuous culture methods and is sufficiently complete to support the cell culture during this process. Perfusion cell culture medium formulations may be richer or more concentrated than base cell culture medium formulations to accommodate the method used to remove the spent medium. Perfusion cell culture medium can be used during both the growth and production phases.

Concentrated cell culture medium can contain some or all of the nutrients necessary to maintain the cell culture; in particular, concentrated medium can contain nutrients identified as or known to be consumed during the course of the production phase of the cell culture. Concentrated medium may be based on just about any cell culture media formulation. Such a concentrated feed medium can contain some or all the components of the cell culture medium at, for example, about 2×, 3×, 4×, 5×, 6×, 7×, 8×, 9×, 10×, 12×, 14×, 16×, 20×, 30×, 50×, 100×, 200×, 400×, 600×, 800×, or even about 1000× their normal amount.

The components used to prepare cell culture medium may be completely milled into a powder medium formulation;

partially milled with liquid supplements added to the cell culture medium as needed; or added in a completely liquid form to the cell culture.

Cell cultures can also be supplemented with independent concentrated feeds of particular nutrients which may be difficult to formulate or are quickly depleted in cell cultures. Such nutrients may be amino acids such as tyrosine, cysteine and/or cystine (see e.g., WIPO Publication No. 2012/145682). In one embodiment, a concentrated solution of tyrosine is independently fed to a cell culture grown in a cell culture medium containing tyrosine, such that the concentration of tyrosine in the cell culture does not exceed 8 mM. In another embodiment, a concentrated solution of tyrosine and cystine is independently fed to the cell culture being grown in a cell culture medium lacking tyrosine, cystine or cysteine. The independent feeds can begin prior to or at the start of the production phase. The independent feeds can be accomplished by fed batch to the cell culture medium on the same or different days as the concentrated feed medium. The independent feeds can also be perfused on the same or different days as the perfused medium.

"Serum-free" applies to a cell culture medium that does not contain animal sera, such as fetal bovine serum. Various tissue culture media, including defined culture media, are commercially available, for example, any one or a combination of the following cell culture media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series (JRH Biosciences, Lenexa, Kans.), among others. Serum-free versions of such culture media are also available. Cell culture media may be supplemented with additional or increased concentrations of components such as amino acids, salts, sugars, vitamins, hormones, growth factors, buffers, antibiotics, lipids, trace elements and the like, depending on the requirements of the cells to be cultured and/or the desired cell culture parameters. The term "bioreactor" means any vessel useful for the growth of a cell culture. The cell cultures of the instant disclosure can be grown in a bioreactor, which can be selected based on the application of a protein of interest that is produced by cells growing in the bioreactor. A bioreactor can be of any size so long as it is useful for the culturing of cells; typically, a bioreactor is sized appropriate to the volume of cell culture being grown inside of it. Typically, a bioreactor will be at least 1 liter and may be 2, 5, 10, 50, 100, 200, 250, 500, 1,000, 1500, 2000, 2,500, 5,000, 8,000, 10,000, 12,000 liters or more, or any volume in between. The internal conditions of the bioreactor, including, but not limited to pH and temperature, can be controlled during the culturing period. Those of ordinary skill in the art will be aware of, and will be able to select, suitable bioreactors for use in practicing the present invention based on the relevant considerations.

"Cell density" refers to the number of cells in a given volume of culture medium. "Viable cell density" refers to the number of live cells in a given volume of culture medium, as determined by standard viability assays (such as trypan blue dye exclusion method).

The term "cell viability" means the ability of cells in culture to survive under a given set of culture conditions or experimental variations. The term also refers to that portion of cells which are alive at a particular time in relation to the total number of cells, living and dead, in the culture at that time.

"Packed cell volume" (PCV), also referred to as "percent packed cell volume" (% PCV), is the ratio of the volume occupied by the cells, to the total volume of cell culture, expressed as a percentage (see Stettler, et al., (2006) Biotechnol Bioeng. December 20:95(6):1228-33). Packed cell volume is a function of cell density and cell diameter; increases in packed cell volume could arise from increases in either cell density or cell diameter or both. Packed cell volume is a measure of the solid content in the cell culture. Solids are removed during harvest and downstream purification. More solids mean more effort to separate the solid material from the desired product during harvest and downstream purification steps. Also, the desired product can become trapped in the solids and lost during the harvest process, resulting in a decreased product yield. Since host cells vary in size and cell cultures also contain dead and dying cells and other cellular debris, packed cell volume is a more accurate way to describe the solid content within a cell culture than cell density or viable cell density. For example, a 2000 L culture having a cell density of $50 \times 10^6$ cells/ml would have vastly different packed cell volumes depending on the size of the cells. In addition, some cells, when in a growth-arrested state, will increase in size, so the packed cell volume prior to growth-arrest and post growth-arrest will likely be different, due to increase in biomass as a result to cell size increase.

"Growth-arrest", which may also be referred to as "cell growth-arrest", is the point where cells stop increasing in number or when the cell cycle no longer progresses. Growth-arrest can be monitored by determining the viable cell density of a cell culture. Some cells in a growth-arrested state may increase in size but not number, so the packed cell volume of a growth-arrested culture may increase. Growth-arrest can be reversed to some extent, if the cells are not in declining health, by adding reversing the conditions that lead to growth arrest.

The term "titer" means the total amount of a polypeptide or protein of interest (which may be a naturally occurring or recombinant protein of interest) produced by a cell culture in a given amount of medium volume. Titer can be expressed in units of milligrams or micrograms of polypeptide or protein per milliliter (or other measure of volume) of medium. "Cumulative titer" is the titer produced by the cells during the course of the culture, and can be determined, for example, by measuring daily titers and using those values to calculate the cumulative titer.

The term "fed-batch culture" refers to a form of suspension culture and means a method of culturing cells in which additional components are provided to the culture at a time or times subsequent to the beginning of the culture process. The provided components typically comprise nutritional supplements for the cells which have been depleted during the culturing process. Additionally or alternatively, the additional components may include supplementary components (e.g., a cell-cycle inhibitory compound). A fed-batch culture is typically stopped at some point and the cells and/or components in the medium are harvested and optionally purified.

The terms "integrated viable cell density" or "IVCD" are used interchangeably and mean the average density of viable cells over the course of the culture multiplied by the amount of time the culture has run.

"Cumulative viable cell density" (CVCD) is calculated by multiplying an average viable cell density (VCD) between two time-points with the time duration between those two time points. CVCD is the area under the curve formed by plotting the VCD versus time.

Description of Cell Culture Process

During recombinant protein production it is desirable to have a controlled system where cells are grown to a desired density and then the physiological state of the cells is switched to a growth-arrested, high productivity state where the cells use energy and substrates to produce the recombinant protein of interest instead of making more cells. Various methods for accomplishing this goal exist, and include temperature shifts and amino acid starvation, as wells as use of a cell-cycle inhibitor or other molecule that can arrest cell growth without causing cell death.

The production of a recombinant protein begins with establishing a mammalian cell production culture of cells that express the protein, in a culture plate, flask, tube, bioreactor or other suitable vessel. Smaller production bioreactors are typically used, in one embodiment the bioreactors are 500 L to 2000 L. In another embodiment, 1000 L-2000 L bioreactors are used. The seed cell density used to inoculate the bioreactor can have a positive impact on the level of recombinant protein produced. In one embodiment the bioreactor is inoculated with at least $0.5 \times 10^6$ up to and beyond $3.0 \times 10^6$ viable cells/mL in a serum-free culture medium. In another embodiment the inoculation is $1.0 \times 10^6$ viable cells/mL.

The mammalian cells then undergo an exponential growth phase. The cell culture can be maintained without supplemental feeding until a desired cell density is achieved. In one embodiment the cell culture is maintained for up to three days with or without supplemental feeding. In another embodiment the culture can be inoculated at a desired cell density to begin the production phase without a brief growth phase. In any of the embodiments herein the switch from the growth phase to production phase can also be initiated by any of the afore-mentioned methods.

At the transition between the growth phase and the production phase, and during the production phase, the percent packed cell volume (% PCV) is equal to or less than 35%. The desired packed cell volume maintained during the production phase is equal to or less than 35%. In one embodiment the packed cell volume is equal to or less than 30%. In another embodiment the packed cell volume is equal to or less than 20%. In yet another embodiment the packed cell volume is equal to or less than 15%. In a further embodiment the packed cell volume is equal to or less than 10%.

The desired viable cell density at the transition between the growth and production phases and maintained during the production phase van be various depending on the projects. It can be decided based on the equivalent packed cell volume from the historical data. In one embodiment, the viable cell density is at least about $10 \times 10^6$ viable cells/mL to $80 \times 10^6$ viable cells/mL. In one embodiment the viable cell density is at least about $10 \times 10^6$ viable cells/mL to $70 \times 10^6$ viable cells/mL. In one embodiment the viable cell density is at least about $10 \times 10^6$ viable cells/mL to $60 \times 10^6$ viable cells/mL. In one embodiment the viable cell density is at least about $10 \times 10^6$ viable cells/mL to $50 \times 10^6$ viable cells/mL. In one embodiment the viable cell density is at least about $10 \times 10^6$ viable cells/mL to $40 \times 10^6$ viable cells/mL. In another embodiment the viable cell density is at least about $10 \times 10^6$ viable cells/mL to $30 \times 10^6$ viable cells/mL. In another embodiment the viable cell density is at least about $10 \times 10^6$ viable cells/mL to $20 \times 10^6$ viable cells/mL. In another embodiment, the viable cell density is at least about $20 \times 10^6$ viable cells/mL to $30 \times 10^6$ viable cells/mL. In another embodiment the viable cell density is at least about $20 \times 10^6$ viable cells/mL to at least about $25 \times 10^6$ viable cells/mL, or at least about $20 \times 10^6$ viable cells/mL.

Lower packed cell volume during the production phase helps mitigate dissolved oxygen sparging problems that can hinder higher cell density perfusion cultures. The lower packed cell volume also allows for a smaller media volume which allows for the use of smaller media storage vessels and can be combined with slower flow rates. Lower packed cell volume also has less impact on harvest and downstream processing, compared to higher cell biomass cultures. All of which reduces the costs associated with manufacturing recombinant protein therapeutics.

Three methods are typically used in commercial processes for the production of recombinant proteins by mammalian cell culture: batch culture, fed-batch culture, and perfusion culture. Batch culture is a discontinuous method where cells are grown in a fixed volume of culture media for a short period of time followed by a full harvest. Cultures grown using the batch method experience an increase in cell density until a maximum cell density is reached, followed by a decline in viable cell density as the media components are consumed and levels of metabolic by-products (such as lactate and ammonia) accumulate. Harvest typically occurs at the point when the maximum cell density is achieved (typically $5$-$10 \times 10^6$ cells/mL, depending on media formulation, cell line, etc). The batch process is the simplest culture method, however viable cell density is limited by the nutrient availability and once the cells are at maximum density, the culture declines and production decreases. There is no ability to extend a production phase because the accumulation of waste products and nutrient depletion rapidly lead to culture decline, (typically around 3 to 7 days).

Fed-batch culture improves on the batch process by providing bolus or continuous media feeds to replenish those media components that have been consumed. Since fed-batch cultures receive additional nutrients throughout the run, they have the potential to achieve higher cell densities (>10 to $30 \times 10^6$ cells/ml, depending on media formulation, cell line, etc)) and increased product titers, when compared to the batch method. Unlike the batch process, a biphasic culture can be created and sustained by manipulating feeding strategies and media formulations to distinguish the period of cell proliferation to achieve a desired cell density (the growth phase) from the period of suspended or slow cell growth (the production phase). As such, fed batch cultures have the potential to achieve higher product titers compared to batch cultures. Typically a batch method is used during the growth phase and a fed-batch method used during the production phase, but a fed-batch feeding strategy can be used throughout the entire process. However, unlike the batch process, bioreactor volume is a limiting factor which limits the amount of feed. Also, as with the batch method, metabolic by-product accumulation will lead to culture decline, which limits the duration of the production phase, about 1.5 to 3 weeks. Fed-batch cultures are discontinuous and harvest typically occurs when metabolic by-product levels or culture viability reach predetermined levels. When compared to a batch culture, in which no feeding occurs, a fed batch culture can produce greater amounts of recombinant protein. See e.g. U.S. Pat. No. 5,672,502.

Perfusion methods offer potential improvement over the batch and fed-batch methods by adding fresh media and simultaneously removing spent media. Typical large scale commercial cell culture strategies strive to reach high cell densities, $60$-$90(+) \times 10^6$ cells/mL where almost a third to over one-half of the reactor volume is biomass. With perfusion culture, extreme cell densities of $>1 \times 10^8$ cells/mL have been achieved and even higher densities are predicted. Typical perfusion cultures begin with a batch culture start-up lasting for a day or two followed by continuous, step-wise and/or intermittent addition of fresh feed media to the culture and simultaneous removal of spent media with the retention of cells and additional high molecular weight compounds such as proteins (based on the filter molecular weight cutoff) throughout the growth and production phases of the culture. Various methods, such as sedimentation, centrifugation, or filtration, can be used to remove spent media, while maintaining cell density. Perfusion flow rates of a fraction of a working volume per day up to many multiple working volumes per day have been reported.

An advantage of the perfusion process is that the production culture can be maintained for longer periods than batch or fed-batch culture methods. However, increased media preparation, use, storage and disposal are necessary to support a long term perfusion culture, particularly those with high cell densities, which also need even more nutrients, and all of this drives the production costs even higher, compared to batch and fed batch methods. In addition, higher cell densities can cause problems during production, such as maintaining dissolved oxygen levels and problems with increased gassing including supplying more oxygen and removing more carbon dioxide, which would result in more foaming and the need for alterations to antifoam strategies; as well as during harvest and downstream processing where the efforts required to remove the excessive cell material can result in loss of product, negating the benefit of increased titer due to increased cell mass.

Also provided is a large scale cell culture strategy that combines fed batch feeding during the growth phase followed by continuous perfusion during the production phase. The method targets a production phase where the cell culture is maintained at a packed cell volume of less than or equal to 35%.

In one embodiment, a fed-batch culture with bolus feeds is used to maintain a cell culture during the growth phase. Perfusion feeding can then be used during a production phase. In one embodiment, perfusion begins when the cells have reached a production phase. In another embodiment, perfusion begins on or about day 3 to on or about day 9 of the cell culture. In another embodiment perfusion begins on or about day 5 to on or about day 7 of the cell culture.

Using bolus feeding during the growth phase allows the cells to transition into the production phase, resulting in less dependence on a temperature shift as a means of initiating and controlling the production phase, however a temperature shift of 36° C. to 31° C. can take place between the growth phase and production phase. In one embodiment the shift is from 36° C. to 33° C. In another embodiment the initiation of cell growth-arrest in the fed-batch culture can be initiated by exposing the fed-batch culture to a cell-cycle inhibitor. In another embodiment the initiation of cell growth-arrest in the fed-batch culture can be achieved by perfusion with a serum free perfusion medium comprising a cell-cycle inhibitor.

As described herein, the bioreactor can be inoculated with at least $0.5 \times 10^6$ up to and beyond $3.0 \times 10^6$ viable cells/mL in a serum-free culture medium, for example $1.0 \times 10^6$ viable cells/mL.

Perfusion culture is one in which the cell culture receives fresh perfusion feed medium while simultaneously removing spent medium. Perfusion can be continuous, step-wise, intermittent, or a combination of any or all of any of these. Perfusion rates can be less than a working volume to many working volumes per day. The cells are retained in the culture and the spent medium that is removed is substantially free of cells or has significantly fewer cells than the culture. Recombinant proteins expressed by the cell culture can also be retained in the culture. Perfusion can be accomplished by a number of means including centrifugation, sedimentation, or filtration, See e.g. Voisard et al., (2003), Biotechnology and Bioengineering 82:751-65. An example of a filtration method is alternating tangential flow filtration. Alternating tangential flow is maintained by pumping medium through hollow-fiber filter modules. See e.g. U.S. Pat. No. 6,544,424; Furey (2002) Gen. Eng. News. 22 (7), 62-63.

"Perfusion flow rate" is the amount of media that is passed through (added and removed) from a bioreactor, typically expressed as some portion or multiple of the working volume, in a given time. "Working volume" refers to the amount of bioreactor volume used for cell culture. In one embodiment the perfusion flow rate is one working volume or less per day. Perfusion feed medium can be formulated to maximize perfusion nutrient concentration to minimize perfusion rate.

Cell cultures can be supplemented with concentrated feed medium containing components, such as nutrients and amino acids, which are consumed during the course of the production phase of the cell culture. Concentrated feed medium may be based on just about any cell culture media formulation. Such a concentrated feed medium can contain most of the components of the cell culture medium at, for example, about 5×, 6×, 7×, 8×, 9×, 10×, 12×, 14×, 16×, 20×, 30×, 50×, 100×, 200×, 400×, 600×, 800×, or even about 1000× of their normal amount. Concentrated feed media are often used in fed batch culture processes.

The method according to the present invention may be used to improve the production of recombinant proteins in multiple phase culture processes. In a multiple stage process, cells are cultured in two or more distinct phases. For example cells may be cultured first in one or more growth phases, under environmental conditions that maximize cell proliferation and viability, then transferred to a production phase, under conditions that maximize protein production. In a commercial process for production of a protein by mammalian cells, there are commonly multiple, for example, at least about 2, 3, 4, 5, 6, 7, 8, 9, or 10 growth phases that occur in different culture vessels preceding a final production culture.

The growth and production phases may be preceded by, or separated by, one or more transition phases. In multiple phase processes, the method according to the present invention can be employed at least during the growth and production phase of the final production phase of a commercial cell culture, although it may also be employed in a preceding growth phase. A production phase can be conducted at large scale. A large scale process can be conducted in a volume of at least about 100, 500, 1000, 2000, 3000, 5000, 7000, 8000, 10,000, 15,000, 20,000 liters. In one embodiment production is conducted in 500 L, 1000 L and/or 2000 L bioreactors.

A growth phase may occur at a higher temperature than a production phase. For example, a growth phase may occur at a first temperature from about 35° C. to about 38° C., and a production phase may occur at a second temperature from about 29° C. to about 37° C., optionally from about 30° C. to about 36° C. or from about 30° C. to about 34° C. In addition, chemical inducers of protein production, such as, for example, caffeine, butyrate, and hexamethylene bisacetamide (HMBA), may be added at the same time as, before, and/or after a temperature shift. If inducers are added after a temperature shift, they can be added from one hour to five days after the temperature shift, optionally from one to two days after the temperature shift. The cell cultures can be maintained for days or even weeks while the cells produce the desired protein(s).

Samples from the cell culture can be monitored and evaluated using any of the analytical techniques known in the art. A variety of parameters including recombinant protein and medium quality and characteristics can be monitored for the duration of the culture. Samples can be taken and monitored intermittently at a desirable frequency, including continuous monitoring, real time or near real time.

Typically the cell cultures that precede the final production culture (N-x to N-1) are used to generate the seed cells that will be used to inoculate the production bioreactor, the N-1 culture. The seed cell density can have a positive impact on the level of recombinant protein produced. Product levels tend to increase with increasing seed density. Improvement in titer is tied not only to higher seed density, but is likely to be influenced by the metabolic and cell cycle state of the cells that are placed into production.

Seed cells can be produced by any culture method. One such method is a perfusion culture using alternating tangential flow filtration. An N-1 bioreactor can be run using alternating tangential flow filtration to provide cells at high density to inoculate a production bioreactor. The N-1 stage may be used to grow cells to densities of $>90 \times 10^6$ cells/mL. The N-1 bioreactor can be used to generate bolus seed cultures or can be used as a rolling seed stock culture that could be maintained to seed multiple production bioreactors at high seed cell density. The duration of the growth stage of production can range from 7 to 14 days and can be designed so as to maintain cells in exponential growth prior to inoculation of the production bioreactor. Perfusion rates, medium formulation and timing are optimized to grow cells and deliver them to the production bioreactor in a state that is most conducive to optimizing their production. Seed cell densities of $>15 \times 10^6$ cells/mL can be achieved for seeding production bioreactors. Higher seed cell densities at inoculation can decrease or even eliminate the time needed to reach a desired production density.

The invention finds particular utility in regulating the presence and/or amount of glycosylation of a recombinant protein. The cell lines (also referred to as "host cells") used in the invention are genetically engineered to express a polypeptide of commercial or scientific interest. Cell lines are typically derived from a lineage arising from a primary culture that can be maintained in culture for an unlimited time. Genetically engineering the cell line involves transfecting, transforming or transducing the cells with a recombinant polynucleotide molecule, and/or otherwise altering (e.g., by homologous recombination and gene activation or fusion of a recombinant cell with a non-recombinant cell) so as to cause the host cell to express a desired recombinant polypeptide. Methods and vectors for genetically engineering cells and/or cell lines to express a polypeptide of interest are well known to those of skill in the art; for example, various techniques are illustrated in *Current Protocols in Molecular Biology*, Ausubel et al., eds. (*Wiley & Sons*, New York, 1988, and quarterly updates); Sambrook et al., Molecular Cloning: A Laboratory Manual (Cold Spring Laboratory Press, 1989); Kaufman, R. J., *Large Scale Mammalian Cell Culture,* 1990, pp. 15-69.

Animal cell lines are derived from cells whose progenitors were derived from a multi-cellular animal. One type of animal cell line is a mammalian cell line. A wide variety of mammalian cell lines suitable for growth in culture are available from the American Type Culture Collection (Manassas, Va.) and commercial vendors. Examples of cell lines commonly used in the industry include VERO, BHK, HeLa, CV1 (including Cos), MDCK, 293, 3T3, myeloma cell lines (e.g., NSO, NS1), PC12, WI38 cells, and Chinese hamster ovary (CHO) cells. CHO cells are widely used for the production of complex recombinant proteins, e.g. cytokines, clotting factors, and antibodies (Brasel et al. (1996), *Blood* 88:2004-2012; Kaufman et al. (1988), *J. Biol Chem* 263: 6352-6362; McKinnon et al. (1991), *J Mol Endocrinol* 6:231-239; Wood et al. (1990), *J. Immunol.* 145:3011-3016). The dihydrofolate reductase (DHFR)-deficient mutant cell lines (Urlaub et al. (1980), *Proc Natl Acad Sci USA* 77: 4216-4220), DXB11 and DG-44, are desirable CHO host cell lines because the efficient DHFR selectable and amplifiable gene expression system allows high level recombinant protein expression in these cells (Kaufman R. J. (1990), *Meth Enzymol* 185:537-566). In addition, these cells are easy to manipulate as adherent or suspension cultures and exhibit relatively good genetic stability. CHO cells and proteins recombinantly expressed in them have been extensively characterized and have been approved for use in clinical commercial manufacturing by regulatory agencies. Proteins of Interest The methods of the invention can be used to culture cells that express recombinant proteins of interest. The expressed recombinant proteins may be secreted into the culture medium from which they can be recovered and/or collected. In addition, the proteins can be purified, or partially purified, from such culture or component (e.g., from culture medium) using known processes and products available from commercial vendors. The purified proteins can then be "formulated", meaning buffer exchanged, sterilized, bulk-packaged, and/or packaged for a final user. Suitable formulations for pharmaceutical compositions include those described in *Remington's Pharmaceutical Sciences,* 18th ed. 1995, Mack Publishing Company, Easton, Pa.

Examples of polypeptides that can be produced with the methods of the invention include proteins comprising amino acid sequences identical to or substantially similar to all or part of one of the following proteins: tumor necrosis factor (TNF), flt3 ligand (WO 94/28391), erythropoeitin, thrombopocitin, calcitonin, IL-2, angiopoietin-2 (Maisonpierre et al. (1997), *Science* 277(5322): 55-60), ligand for receptor activator of NF-kappa B (RANKL, WO 01/36637), tumor necrosis factor (TNF)-related apoptosis-inducing ligand (TRAIL, WO 97/01633), thymic stroma-derived lymphopoietin, granulocyte colony stimulating factor, granulocyte-macrophage colony stimulating factor (GM-CSF, Australian Patent No. 588819), mast cell growth factor, stem cell growth factor (U.S. Pat. No. 6,204,363), epidermal growth factor, keratinocyte growth factor, megakaryote growth and development factor, RANTES, human fibrinogen-like 2 protein (FGL2; NCBI accession no. NM_00682; Rüegg and Pytela (1995). *Gene* 160:257-62) growth hormone, insulin, insulinotropin, insulin-like growth factors, parathyroid hormone, interferons including α-interferons, γ-interferon, and consensus interferons (U.S. Pat. Nos. 4,695,623 and 4,897, 471), nerve growth factor, brain-derived neurotrophic factor, synaptotagmin-like proteins (SLP 1-5), neurotrophin-3, glucagon, interleukins, colony stimulating factors, lymrphotoxin-β, leukemia inhibitory factor, and oncostatin-M. Descriptions of proteins that can be produced according to the inventive methods may be found in, for example, *Human Cytokines: Handbook for Basic and Clinical Research, all volumes* (Aggarwal and Gutterman, eds. Blackwell Sciences, Cambridge, Mass., 1998); *Growth Factors: A Prac-* tical Approach (McKay and Leigh, eds., Oxford University Press Inc., New York, 1993); and *The Cytokine Handbook*, Vols. 1 and 2 (Thompson and Lotze eds., Academic Press, San Diego, Calif., 2003).

Additionally the methods of the invention would be useful to produce proteins comprising all or part of the amino acid sequence of a receptor for any of the above-mentioned proteins, an antagonist to such a receptor or any of the above-mentioned proteins, and/or proteins substantially similar to such receptors or antagonists. These receptors and antagonists include: both forms of tumor necrosis factor receptor (TNFR, referred to as p55 and p75, U.S. Pat. Nos. 5,395,760 and 5,610,279). Interleukin-1 (IL-1) receptors (types I and II; EP Patent No. 0460846, U.S. Pat. Nos. 4,968,607, and 5,767,064), IL-1 receptor antagonists (U.S. Pat. No. 6,337,072), IL-1 antagonists or inhibitors (U.S. Pat. Nos. 5,981,713, 6,096,728, and 5,075,222) IL-2 receptors, IL-4 receptors (EP Patent No. 0 367 566 and U.S. Pat. No. 5,856,296), IL-15 receptors, IL-17 receptors, IL-18 receptors, Fc receptors, granulocyte-macrophage colony stimulating factor receptor, granulocyte colony stimulating factor receptor, receptors for oncostatin-M and leukemia inhibitory factor, receptor activator of NF-kappa B (RANK, WO 01/36637 and U.S. Pat. No. 6,271,349), osteoprotegerin (U.S. Pat. No. 6,015,938), receptors for TRAIL (including TRAIL receptors 1, 2, 3, and 4), and receptors that comprise death domains, such as Fas or Apoptosis-Inducing Receptor (AIR).

Other proteins that can be produced using the invention include proteins comprising all or part of the amino acid sequences of differentiation antigens (referred to as CD proteins) or their ligands or proteins substantially similar to either of these. Such antigens are disclosed in *Leukocyte Typing VI* (*Proceedings of the 17th International Workshop and Conference*, Kishimoto, Kikutani et al., eds., Kobe, Japan, 1996). Similar CD proteins are disclosed in subsequent workshops. Examples of such antigens include CD22, CD27, CD30, CD39, CD40, and ligands thereto (CD27 ligand, CD30 ligand, etc.). Several of the CD antigens are members of the TNF receptor family, which also includes 41BB and OX40. The ligands are often members of the TNF family, as are 41BB ligand and OX40 ligand.

Enzymatically active proteins or their ligands can also be produced using the invention. Examples include proteins comprising all or part of one of the following proteins or their ligands or a protein substantially similar to one of these: a disintegrin and metalloproteinase domain family members including TNF-alpha Converting Enzyme, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, ligands for any of the above-mentioned enzymes, and numerous other enzymes and their ligands.

Examples of antibodies that can be produced include, but are not limited to, those that recognize any one or a combination of proteins including, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-1 receptor, IL-2 receptor, IL-4 receptor, IL-6 receptor, IL-13 receptor, IL-18 receptor subunits, FGL2, PDGF-β and analogs thereof (see U.S. Pat. Nos. 5,272,064 and 5,149,792), VEGF, TGF, TGF-β2, TGF-β1, EGF receptor (see U.S. Pat. No. 6,235,883) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), *Cytokine Growth Factor Rev.* 13(1): 19-25), C5 complement, IgE, tumor antigen CA125, tumor antigen MUC1, PEM antigen, LCG (which is a gene product that is expressed in association with lung cancer), HER-2, HER-3, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, integrins (including integrins comprising alpha4beta7), TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor Vila-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, sclerostin, L-selectin, Respiratory Syncitial Virus, human immunodeficiency virus (HIV), hepatitis B virus (HBV), *Streptococcus mutans*, and *Staphlycoccus aureus*.

Specific examples of known antibodies which can be produced using the methods of the invention include but are not limited to adalimurnab, bevacizumab, infliximab, abciximab, alemtuzumab, bapineuzumab, basiliximab, belimumab, briakinumab, brodalumab, canakinumab, certolizumab pegol, cetuximab, conatumumab, denosumab, eculizumab, germtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ramibizumab, rituximab, rovelizumab, tocilizumab, tositumomab, trastuzumab, ustekinunab, vedolizomab, zalutunumab, and zanolimumab.

The invention can also be used to produce recombinant fusion proteins comprising, for example, any of the above-mentioned proteins. For example, recombinant fusion proteins comprising one of the above-mentioned proteins plus a multimerization domain, such as a leucine zipper, a coiled coil, an Fe portion of an immunoglobulin, or a substantially similar protein, can be produced using the methods of the invention. See e.g. WO94/10308; Lovejoy et al. (1993), *Science* 259:1288-1293; Harbury et al. (1993), *Science* 262:1401-05; Harbury et al. (1994), *Nature* 371:80-83; Hakansson et al. (1999), *Structure* 7:255-64. Specifically included among such recombinant fusion proteins are proteins in which a portion of a receptor is fused to an Fe portion of an antibody such as etanercept (a p75 TNFR:Fc), abatacept and belatacept (CTLA4:Fc).

The present invention is not to be limited in scope by the specific embodiments described herein that are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

EXAMPLES

Example 1

The effect of monensin on high mannose glycans in a recombinant CHO cell line producing an antibody (MAb A) that exhibits very low levels of high mannose glycans was assessed in a six day batch assay. Cells were centrifuged at 1500 rpm for five minutes and seeded at $2 \times 10^6$ cells per ml into batch production medium in a 24 deep-well plate at a final volume of 3 ml. Stock solutions of monensin (1000×; eBiosciences Inc., San Diego, Calif.) were prepared in methanol and added to the cultures at different concentrations and at different time points during the assay (0.1 nM to 50 nM on day 1 and 100-500 nM on day 3); methanol was added as vehicle control.

Cell culture parameters were analyzed on day 6 and the corresponding spent medium supernatants were evaluated for antibody titer and glycan analysis to assess the effect of monensin on cell growth, viability, titer and glycan profile of the recombinant antibody. Cell density and viability were measured by Guava easyCyte flow cytometer (Milipore, Billerica, Mass.) with the ViaCount application. Cultures were spun down, supernatants were filtered on 0.4 micron filters, and were analyzed for titer and glycan distribution.

Antibody titer was measured by loading filtered cell culture supernatants over a POROS A/20 Protein A column (Applied Biosystems, Carlsbad, Calif.) equilibrated with 20 mM Tris, 150 nM NaCl, pH 7.0 buffer. Antibody elution was performed with 220 mM acetic acid, 150 nM NaCl, pH 2.6 buffer at a mobile phase flow rate of 4.0 ml/min. Eluted antibody was detected at a wavelength of 280 nm. Antibody concentration was determined based on a standard curve with a reference antibody standard. For high molecular weight measurement, antibodies were purified from spent medium supernatants on ATOLL columns (ATOLL-Bio Inc USA, Lawrance, Kans.) and were then analyzed using size exclusion chromatography.

For glycan analysis, Peptide-N-Glycosidase F (PNGAse F)—released N-linked glycans from protein A purified antibodies were labeled with 2-aminobenzoic acid (2-AA) and separated by HILIC (hydrophilic interaction liquid chromatography) in-line with a fluorescence detector. The separation was performed using a Waters Acquity UPLC (Waters, Milford, Mass.). In-line mass spectrometry (MS), using an ion trap mass spectrometer (LTQ; Thermo Scientific, Waltham, Mass.) in positive mode, was incorporated to accommodate mass determination of species. Glycans were injected and bound to the column in high organic conditions and were then eluted with an increasing gradient of an aqueous ammonium formate buffer. Fast separation times were achieved using a 1.7 microM small particle column format (Acquity UPLC BEH Glycan Column, 2.1×100 mm; Waters, Milford, Mass.).

Monensin caused a dose dependent increase in high mannose glycans on the recombinant antibody as shown in Table 1. Man5 was the major high mannose species upregulated upon monensin treatment, though there was a slight increase in higher order mannose structures as well. At monensin concentrations between 0.1 to 10 nM, there were no impacts on high mannose or cell culture parameters. At high concentrations (50 nM incubated for six days and 500 nM incubated for three days), monensin caused large increases in high mannose at the expense of cell growth, viability and titer. However, when administered as a 25 nM bolus on day 0 or either a 200 nM or 100 nM bolus on day 3, monensin increased total high mannose glycans on the recombinant antibody anywhere from 6 to 30-fold with no negative impact on cell culture parameters. Methanol, which was used as a vehicle control, did not increase high mannose glycans.

TABLE 1

Levels of various glycans

| Average | Total HM | Man5 (%) | Man6 (%) | Man7 (%) | Man8a (%) | Man8b (%) |
|---|---|---|---|---|---|---|
| Control | 1.25 | 0.785 | 0.06 | 0.43 | 0.305 | 0 |
| Methanol | 0.65 | 0.655 | 0 | 0 | 0.375 | 0 |
| 50 nM | 25.1 | 15.725 | 4.64 | 4.73 | 0.8 | 2.02 |
| 25 nM | 7.65 | 6.43 | 0.59 | 0.59 | 0.39 | 0.115 |
| 10 nM | 1.6 | 1.485 | 0.16 | 0 | 0.315 | 0 |
| 5 nM | 1.35 | 1.12 | 0.18 | 0.27 | 0.37 | 0 |
| 1 nM | 1.05 | 0.89 | 0.13 | 0.04 | 0.29 | 0 |
| 0.5 nM | 0.85 | 0.785 | 0.07 | 0 | 0.3 | 0 |
| 0.1 nM | 0.8 | 0.775 | 0.09 | 0 | 0.31 | 0 |
| 500 nM(d 3) | 14.3 | 11.735 | 1.545 | 1.045 | 0.355 | 0.2 |
| 200 nM(d 3) | 27.35 | 18.585 | 4.975 | 3.795 | 0.61 | 1.17 |
| 100 nM(d 3) | 33.65 | 19.365 | 7.475 | 6.795 | 0.8 | 2.635 |

Cell culture performance was assessed via viable cell density (VCD), viability and titer measurements of harvested samples. Each bar represents an average result for duplicate cell culture samples. Each value is an average of duplicates.

TABLE 2

Cell culture parameters

| Average | VCD ($10^6$ c/ml) | Viability (%) | Titer (g/L) |
|---|---|---|---|
| Control | 11 | 79 | 3.76 |
| Methanol | 10 | 80 | 3.835 |
| 50 nM | 5 | 72 | 2.025 |
| 25 nM | 11 | 85 | 5.22 |
| 10 nM | 11 | 81 | 3.635 |
| 5 nM | 11 | 82 | 3.45 |
| 1 nM | 11 | 82 | 4.265 |
| 0.5 nM | 11 | 81 | 4.415 |
| 0.1 nM | 10 | 81 | 3.835 |
| 500 nM(d 3) | 5 | 41 | 3.055 |
| 200 nM(d 3) | 11 | 87 | 4.43 |
| 100 nM(d 3) | 11 | 86 | 3.515 |

Taken together these results indicated that monensin has a potential to be used to increase high mannose glycans on recombinant therapeutic antibodies with no negative impacts on product yield.

Example 2

The effect of monensin on various antibody production cell lines was evaluated in a mock perfusion setting. Mock perfusion assay is a small scale, plate-based assay that is designed to mimic perfusion conditions in bioreactors through daily medium exchanges. For a 10-day mock perfusion assay, passaging cultures of various production cell lines were diluted 1:5 into chemically defined base perfusion medium in a 24 deep-well plate at a final volume of 3 ml per well. Mock perfusion was initiated on day 3 when the cells were spun down at 1000 rpm for 5 minutes and 25% of each spent culture medium was exchanged with the equivalent volume of fresh perfusion media. Subsequent medium exchange percentages were 40% on days 4-8 and 50% on day 9. Exchanged supernatants were stored at 4° C. prior to analysis.

Analysis of cell culture parameters was also started on day 3; viable cell density and viability were analyzed using the ViaCount Guava assay as previously described. Glucose was measured daily starting on day 3 and was maintained at 12 g/l. Stored supernatants were analyzed for antibody titer as described previously. Samples of supernatant fluid from days 6, 8 and 10 were also analyzed for the presence and type of glycans by HILIC analysis.

The cell lines used included three production cell lines that are known to generate mAbs with low high mannose glycans (MAb A, MAb B and MAb C) and one production cell line that consistently produces product with high levels of high mannose glycans (MAb D). Monensin was added at a final concentration of 25 nM on day 3 and from then on one set of duplicate samples underwent daily partial medium exchanges with perfusion medium containing 25 nM monensin (referred to as "Constant Monensin" in Table 3 below; columns 3 and 4 of the 24-well plate). Another set of duplicate samples received perfusion medium with increasing doses of monensin (referred to as "Increasing Monensin" in Table 3 below; columns 5 and 6 of the 24-well plate). Equivalent volumes of methanol were added daily to control cultures (columns 1 and 2 of the 24-well plate). This scheme is depicted below:

|  | Columns 1 and 2 | Columns 3 and 4 | Columns 5 and 6 |
| --- | --- | --- | --- |
| Row 1: Cells producing MAb A | Control: Perfused at 40% of initial volume with media containing equal volume of methanol on days 4, 5,6,7,and 8, and 50% on 9 | Constant monensin: Perfused at 40% of initial volume with media containing 25 nM monensin on days 4, 5,6,7, and 8, and 50% on 9 | Increasing monensin: Perfused at 40% of initial volume with media containing varying monensin on days 4 (25 nM); 5-9 (50 nM; 50% volume perfused on day 9) |
| Rows 2-4: Cells producing MAb B, C, D, respectively | Control: Perfused at 40% of initial volume with media containing equal volume of methanol on days 4, 5,6,7, and 8, and 50% on 9 | Constant monensin: Perfused at 40% of initial volume with media containing 25 nM monensin on days 4, 5,6,7, and 8, and 50% on 9 | Increasing monensin: Perfused at 40% of initial volume with media containing varying monensin on days 4 (25 nM), 5 and 6 (50 nM), 7, 8 and 9 (100 nM; 50% volume perfused on day 9) |

On day 10, cell pellets were washed once with cold PBS and fixed in 4% paraformaldehyde for 10 minutes on ice. Cells were then washed once in again in cold PBS and stored at 4° C. until they were immunofluorescently stained as described below Similar to results obtained with six day batch assay, monensin increased high mannose glycans on all four antibody products tested in a dose dependent manner though the magnitude of upregulation was cell line dependent, as shown in Table 3.

TABLE 3

| Levels of various glycans | | | |
| --- | --- | --- | --- |
|  | Total HM (%) Day 6 | Total HM (%) Day 8 | Total HM (%) Day 10 |
| MAb A | | | |
| Control | 1.5 | 1.6 | 1.4 |
| Constant monensin | 55.7 | 19.7 | 9 |

TABLE 3-continued

| Levels of various glycans | | | |
| --- | --- | --- | --- |
|  | Total HM (%) Day 6 | Total HM (%) Day 8 | Total HM (%) Day 10 |
| Increasing monensin | 61.9 | 44.9 | 23.2 |
| MAb B | | | |
| Control | 3.0 | 2.8 | 2.8 |
| Constant monensin | 9.6 | 4.6 | 4.0 |
| Increasing monensin | 13.2 | 12.4 | 14.0 |
| MAb C | | | |
| Control | 4.6 | 4.7 | 7.7 |
| Constant monensin | 49.6 | 31.1 | 30.9 |
| Increasing monensin | 56.6 | 67.6 | 65.8 |
| MAb D | | | |
| Control | 18.4 | 26.8 | 32.2 |
| Constant monensin | 70.6 | 80.1 | 72.6 |

TABLE 3-continued

| Levels of various glycans | | | |
| --- | --- | --- | --- |
|  | Total HM (%) Day 6 | Total HM (%) Day 8 | Total HM (%) Day 10 |
| Increasing monensin | 83.0 | 92.5 | 94.9 |

When compared to the control samples, high mannose levels on antibodies collected on day 10 of the production assay exhibited increases of anywhere from 1.5 to 15-fold depending on the monensin dose. The levels of high mannose glycans decreased over time in cultures that were subjected to partial daily medium exchange, starting on day 3, with perfusion medium containing 25 nM monensin, but were higher than control cultures at all time points (Table 3, values shown in rows designated "Constant monensin"). This is likely due to increases in cell number with time, thus reducing the per cell dose of monensin at later time points.

For one of the cell lines, monensin dose in the perfusion medium was ramped up to 50 nM over the course of the production assay run; for the remaining cell-lines, monensin dose in the perfusion medium was ramped up (increased) to 100 nM. As a result of the increasing monensin concentration, high mannose levels on the antibodies produced by these cell lines were held steady from early to later time points (Table 3, values shown in rows designated "Increasing monensin"). For the cell line expressing MAb A (evaluated in Example 1), monensin concentration in the perfusion medium was not increased beyond 50 nM due to the previously observed deleterious effects on cell culture parameters. As such, and similarly to what was observed with 25 nM addition condition, high mannose levels on antibodies produced by that cell-line decreased with time.

Total high mannose values (Total HM column) and the corresponding distributions into high mannose species from Man5 through Man9 were determined for purified antibody samples collected on day 10. Each value shown in Table 4 represents an average of duplicates.

TABLE 4

Levels of various glycans

| | Total HM (%) | Man5 (%) | Man6 (%) | Man7 (%) | Man8a (%) | Man8b (%) | Man9 (%) |
|---|---|---|---|---|---|---|---|
| MAb A | | | | | | | |
| Control | 1.4 | 0.7 | 0.1 | 0.1 | 0.3 | 0.1 | 0.0 |
| Constant Monensin | 9 | 5.6 | 1.2 | 1.0 | 0.4 | 0.6 | 0.2 |
| Increasing monensin | 23.2 | 14.2 | 3.7 | 1.9 | 0.6 | 1.4 | 0.4 |
| MAb B | | | | | | | |
| Control | 2.8 | 1.3 | 0.5 | 0.4 | 0.4 | 0.3 | 0.0 |
| Constant Monensin | 4.0 | 2.2 | 0.7 | 0.5 | 0.3 | 0.3 | 0.0 |
| Increasing monensin | 14.0 | 7.7 | 3.0 | 2.0 | 0.3 | 0.9 | 0.1 |
| MAb C | | | | | | | |
| Control | 7.7 | 4.5 | 1.3 | 0.8 | 0.7 | 0.3 | 0.1 |
| Constant Monensin | 30.9 | 19.5 | 5.3 | 3.6 | 0.7 | 1.4 | 0.3 |
| Increasing monensin | 65.8 | 31.6 | 13.7 | 12.3 | 1.0 | 5.9 | 1.3 |
| MAb D | | | | | | | |
| Control | 32.2 | 20.6 | 4.3 | 3.8 | 0.6 | 2.6 | 0.3 |
| Constant Monensin | 72.6 | 30.4 | 14.7 | 15.3 | 0.7 | 10.1 | 1.4 |
| Increasing monensin | 94.9 | 12.8 | 14.9 | 27.2 | 0.8 | 34.3 | 5.0 |

In most cases monensin elevated the level of high mannose species without changing their relative distribution (i.e. if Man5 was the primary high mannose form prior to monensin addition, it typically stayed the predominant form after monensin administration).

The only exception to this effect was seen on one cell line, that producing MAb D. The increasing dose of monensin primarily upregulated Man7 and Man8(b) high mannose glycans on the mAbs produced by this cell line. This cell line has (in these experiments and in the past) consistently produced mAbs with high levels of high mannose glycans even under control culture conditions. The difference in the upregulation of high mannose species in the presence of monensin in this cell-line when compared to the other tested cell lines could reflect a fundamental difference in high mannose processing machinery in these cells.

Example 3

Monensin is known to cause gross changes in Golgi architecture characterized by swollen and fragmented cisternae. The structure of the Golgi of CHO production cell lines after monensin treatment was analyzed using a panel of five different commercially available antibodies against various Golgi proteins with a passaging culture of recombinant cells producing MAb A using immunofluorescence microscopy. Only the antibody against GM130, a Golgi matrix protein, showed a Golgi specific staining pattern.

Next, day 10 control and monensin-treated mock perfusion cultures of MAb A producing cells and MAb C producing cells were subjected to immunofluorescence microscopy using GM130 antibody. Paraformaldehyde fixed cell pellets were permeablized with 0.1% TritonX-100 made in PBS. Pellets were washed with PBSA (0.5% BSA in PBS) and incubated with GM130 antibody (BD Biosciences, San Jose, Calif.) diluted 1:50 in PBSA. Cells were washed thrice with PBSA and incubated with Alexa 488 conjugated mouse secondary antibody (Invitrogen, Grand Island, N.Y.) diluted 1:1000 in PBSA. Nuclear DNA was visualized with DRAQ5 (Invitrogen, Grand Island, N.Y.). Images were captured using Zeiss 510 microscope (Carl Zeiss, Inc., Jena, Germany) with 63× water immersion lens and analyzed using LSM image browser software.

No morphological difference were observed between control and monensin-treated MAb A-producing cells. However, MAb C producing cells treated with perfusion medium containing continuously increasing amounts of monensin, culminating at 100 nM final monensin concentration in the perfusion medium from days 7-10, showed punctate distribution of GM130 protein perhaps indicative of Golgi stress. This kind of change in staining pattern of GM130 has previously been linked to arsenite or heat shock induced cell stress in HeLa cells (Kolobova, E., et al., Exp Cell Res, 2009; 315(3) 542-55).

The effects of either constant levels of monensin or increasing levels of monensin on various cell culture parameters was also evaluated. Viable cell density (VCD) and viability were measured daily starting on day 3. Spent medium samples were collected on days 3-10 and were subjected to titer analysis. Viable cell densities were used to calculate cumulative viable cell densities, which were along with cumulative titer values used to calculate specific productivities (qP). Every value shown is an average of duplicates. There was no drop in titer or any other negative cell culture impacts in these cells, despite the apparent loss of Golgi morphology, as shown in Table 5.

TABLE 5

Cell culture parameters

| | CVCD ($10^6$ c-day/ml) | End of Production Viability (%) | Cumulative Titer (g/L) | qP (pg/c/d) |
|---|---|---|---|---|
| MAb A | | | | |
| Control | 85 | 85 | 7.5 | 88 |
| Constant Monensin | 57 | 78 | 5.9 | 103 |
| Increasing monensin | 57 | 80 | 5.8 | 101 |

TABLE 5-continued

Cell culture parameters

|  | CVCD (10⁶ c-day/ml) | End of Production Viability (%) | Cumulative Titer (g/L) | qP (pg/c/d) |
|---|---|---|---|---|
| MAb B |  |  |  |  |
| Control | 95 | 85 | 3.6 | 38 |
| Constant Monensin | 89 | 85 | 3.5 | 40 |
| Increasing monensin | 88 | 83 | 3.6 | 40 |
| MAb C |  |  |  |  |
| Control | 192 | 69 | 7.3 | 38 |
| Constant Monensin | 215 | 77 | 7.4 | 34 |
| Increasing monensin | 208 | 77 | 7.1 | 34 |
| MAb D |  |  |  |  |
| Control | 129 | 68 | 5.2 | 40 |
| Constant Monensin | 104 | 68 | 4.5 | 43 |
| Increasing monensin | 89 | 53 | 3.6 | 41 |

The effect of monensin on cell culture parameters under mock perfusion conditions was cell line specific, with MAb A cells exhibiting a decrease in total cell mass accumulation followed by a similar, though not as pronounced, negative growth impact on MAb D cells. Monensin had no effect on the growth or viability of MAb B cells and slightly increased cumulative viable cell density and improved the viability of MAb C cells.

Monensin has a different effect on cell growth and viability depending on production cell line in question. Monensin has been reported to cause G1/S or G2/M cell cycle block and induce apoptosis in certain lymphoma and renal cancer cells lines. It was shown to decrease the level of several cell cycle related proteins like CDK2, CD6, cyclin A and cyclinB1 and to increase the levels of cell cycle inhibitors p21 and p27 (Park, W. H., et al., *Int J Oncol.* 2003, 22(4): 855-60; Park, W. H., et al., *Int J Oncol.* 2003, 23(1): 197-204; Park, W. H., et al., *Br J Haematol.* 2002, 119(2): p. 400-7). The effect of monensin on these cell cycle proteins could explain the negative effect of monensin on MAb A and MAb D cell growth and viability.

On the other hand, low doses of monensin have been reported to improve cell culture parameters by increasing intracellular Na⁺ levels which could explain the improved cell culture performance of MAb C cells in the presence of monensin (Tenaglia, A. N., C. G. Fry, and G. Van Zant, *Exp Hematol.* 1985. 13(6): 512-519). Why different production cell-lines respond differently to monensin is not known and could in part be explained by the heterogeneity of the cells from which these clonal cell lines were derived.

Figure 3:
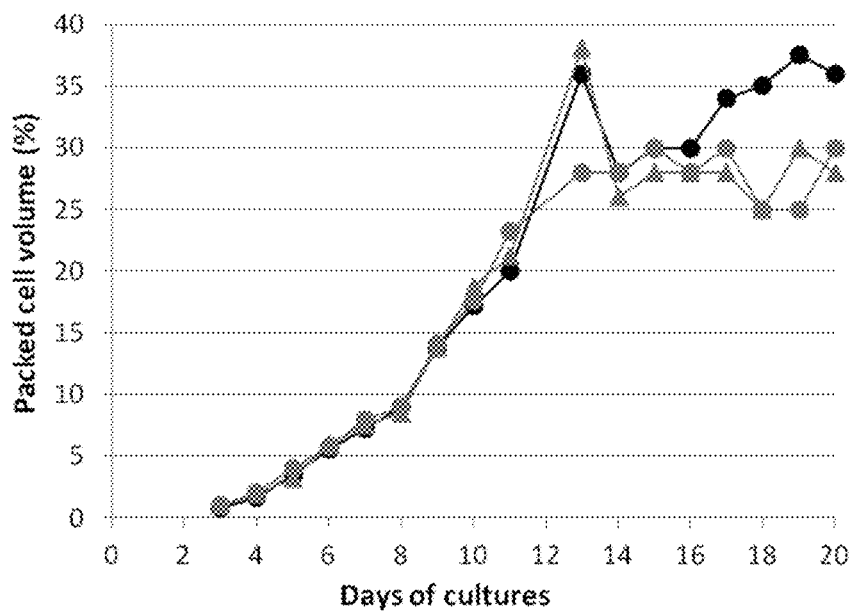
Figure 4:
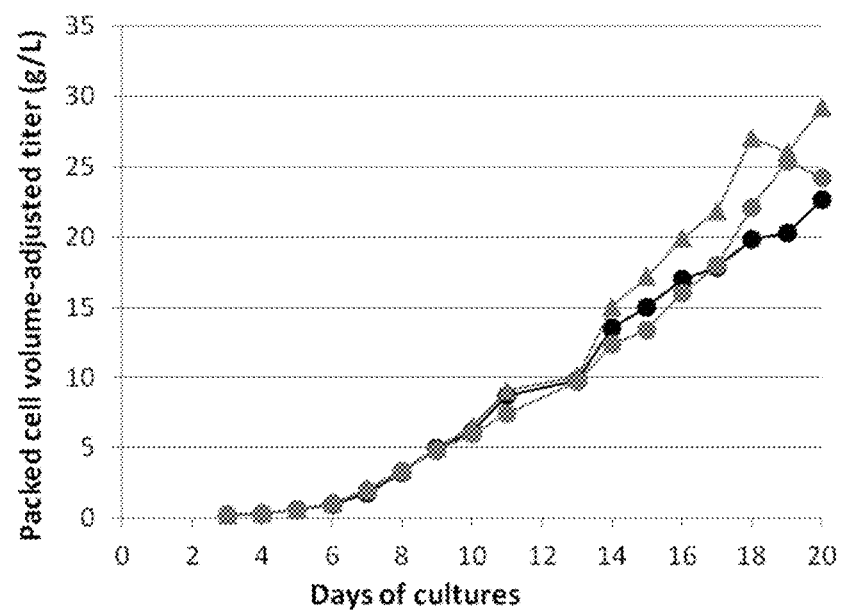
Figure 5:
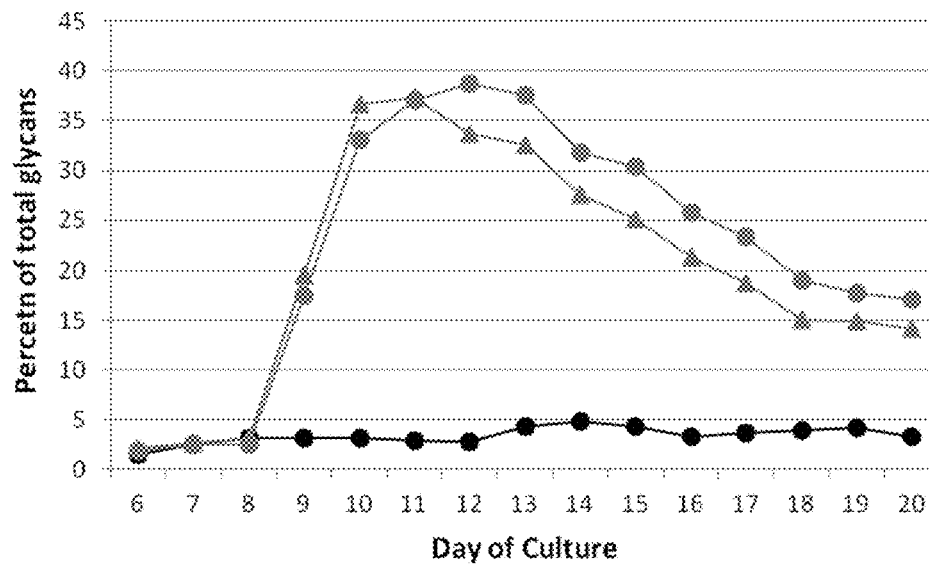
FIGS. 5-8 represent the high mannose profiles of MAb E produced in ATFs in the presence of monensin. As described for FIG. 1-4, monensin concentration in ATF reactors Ra and Rb was held at 500 nM over the course of ~22 hours starting on day 8 and ending on day 9. Daily spent medium samples were submitted for analysis of total high mannose glycans. The total glycan analysis for the spent media samples is shown in FIG. 5 (Ra—gray triangles, Rb—gray circles, control (no monensin)—black circles). In addition to total high mannose, the individual higher order mannose species were analyzed; results are shown in FIG. 6 for the ATF control (no monensin) reactor (total high mannose, black circles; Man5 (black diamonds), Man6 (black triangles), Man7 (black asterisk), Man8 (black square), Man9 (black line).
Figure 6:
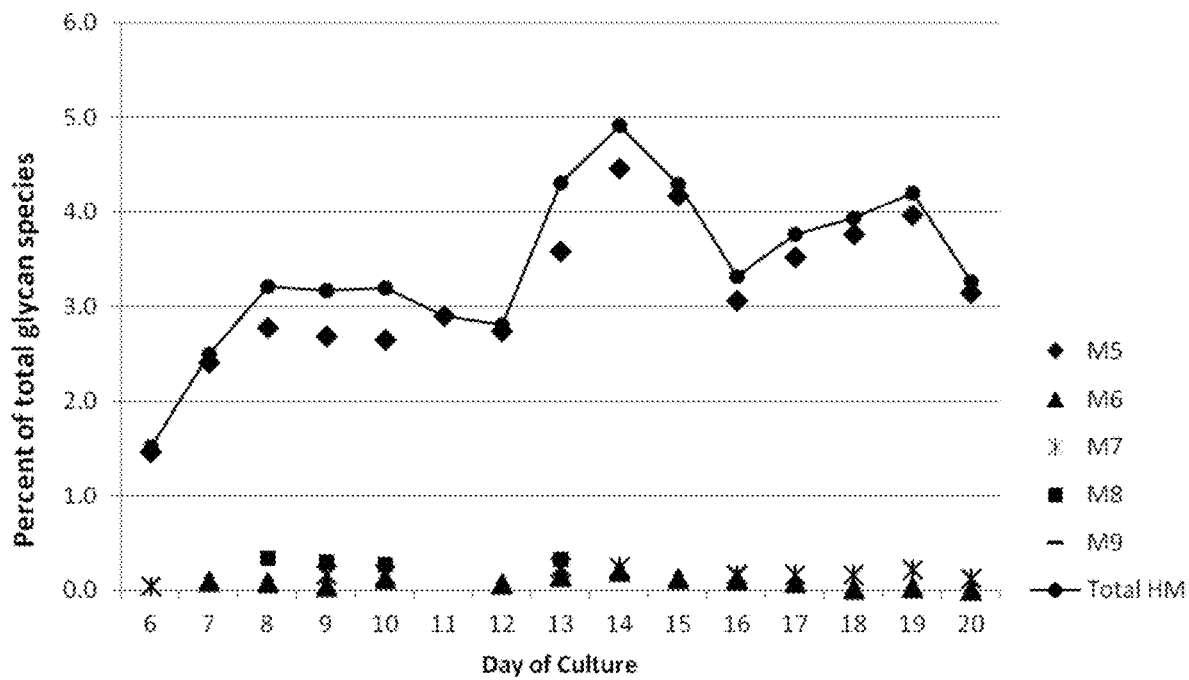
Figure 7:
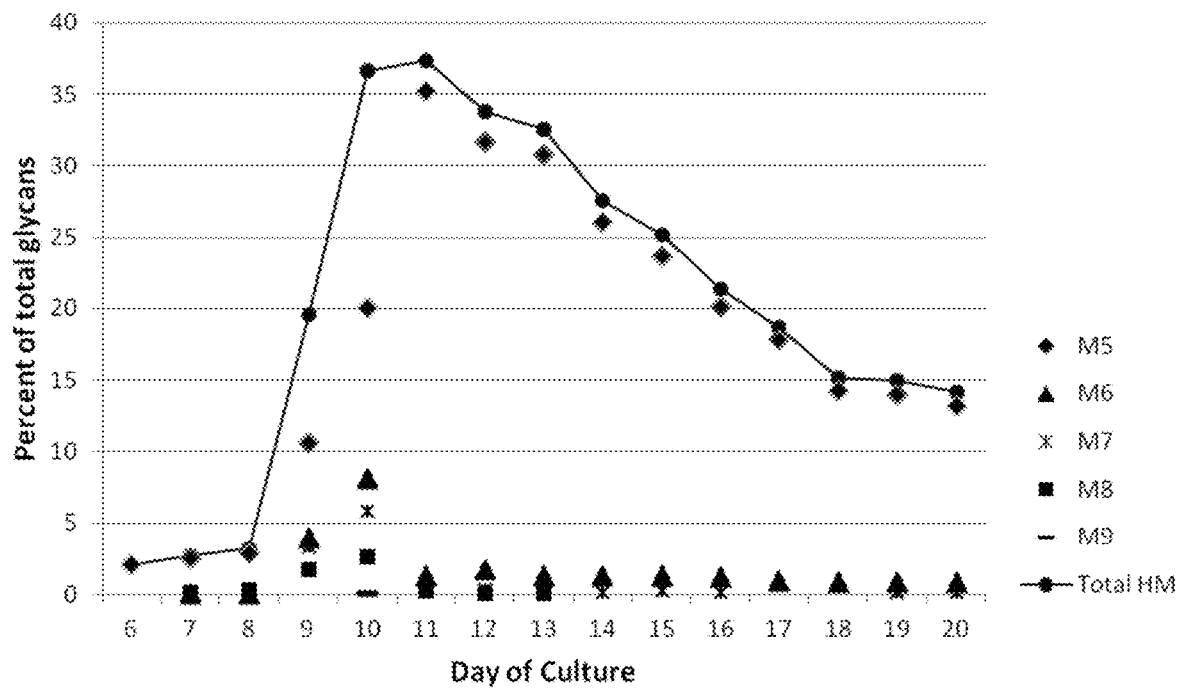
Figure 8:
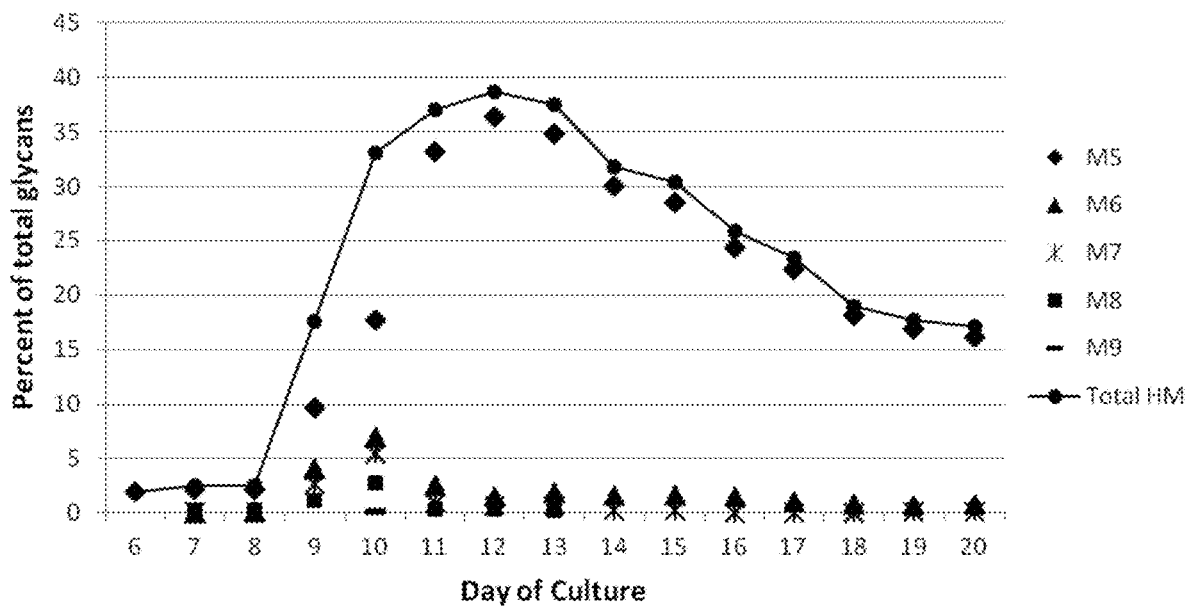

The effect of monensin on titer and specific productivity was also cell line specific (FIG. 3). MAb A cells showed decreased titer but increased specific productivity whereas MAb C cells showed increased titer but slightly lower specific productivity in the presence of monensin. Monensin had no impact on either titer or specific productivity of MAb B cells and slightly decreased the titer of MAb D cells but had no effect on specific productivity. This effect on titer and specific productivity likely reflects the effect monensin has on cell growth and viability. In general however, the use of monensin will facilitate large increases in high mannose glycans without significant effects on titer or specific productivity, and virtually no changes in high molecular weight profiles of antibodies produced.

Example 4

The applicability of using monensin to modulate high mannose levels in a large scale, controlled production setting was evaluated using a recombinant cell line producing MAb E in alternating tangential flow (ATF) bioreactors. MAb E cells grown in growth medium for the seed train were used to inoculate the N-1 bioreactor at $6\times10^5$ cells/ml in growth medium. The cells from N-1 bioreactor were then used to inoculate three, 2 L production bioreactors (N) at $7.5\times10^5$ cells/ml in base perfusion medium (referred to as control, Ra, and Rb bioreactors).

The production bioreactors were grown for 20 days at pH 7.00, 36° C., 30% DO and 400 rpm agitation. These production tanks were run with the ATF system starting on day 3 with 0.5 vol/day perfusion rate, which was increased to 0.6 vol/day, 0.8352 vol/day and 1 vol/day on day 6, 7 and 8, respectively. Glucose levels were maintained separately at 5 g/L since the perfusion medium was prepared without glucose.

Monensin (25 microM stock solution) was added as a single bolus dose to achieve a final concentration of 500 nM into two tanks (Ra and Rb) on day 8; the third tank served as a control tank. Thereafter monensin was fed continuously for roughly 22 hours at a rate of 1/50 of the perfusion medium rate to maintain 500 nM concentration in the tanks. Antifoam was also added into the tank as needed, while 1M Sodium Carbonate was used to maintain pH at the desired setpoint. Daily tank samples were collected for the measurement of various cell culture parameters as well as for the titer and high mannose analyses.

Sixty micrograms of daily MAb E samples collected from ATF bioreactors were digested into the Fc/2 and Fab'2 with 60 units of the IdeS enzyme (fabRICATOR, Genovis, Lund, Sweden) in 50 mM Sodium Phosphate, 150 mM NaCl, pH 6.6 with incubation in a 37° C. water bath for 30 minutes. The digested samples were then reduced in 4M Guanidine Hydrochloride 50 mM Tris, pH 8.3 with 50 mM DTT followed by incubation in a 55° C. heat block for 10 minutes resulting in reduction to Fc/2, LC and Fd.

Following digestion and reduction, samples were analyzed immediately by RP-HPLC/MS.

Analysis was performed using Waters Acquity Ultra-Performance liquid chromatography (UPLC) system (Waters, Milford, Mass.) coupled to an Agilent MST Time of Flight (TOF) mass spectrometer (Agilent Technologies, Santa Clara, Calif.). The digested and reduced samples were separated on a reversed-phased Waters BEH Phenyl column (1.7 micron particle size, 2.1×150 mm; Waters, Milford, Mass.) maintained at 80° C. The mobile phases employed for separation were 0.1% TFA (Buffer A) and Acetonitrile, 0.1% TFA (Buffer B).

Five micrograms of each sample was injected and eluted at a flow rate of 0.5 mL/min with the following gradient: 30% B was held for 2.5 minutes followed by a gradient from 30% to 45% B over a duration of 5 minutes, followed by a gradient from 45% to 100% B over 0.5 minutes; B was held at 100% for 4 minutes, followed by a gradient of 100% to 30% B over 0.1 minutes, and then held at 30% B for the remaining 2.9 minutes. The UV elution was also monitored at a wavelength of 220 nm. Mass data were extracted from the TIC of the FC/2 peak, followed by deconvolution of the extracted spectra using Agilent MassHunter deconvolution software. Ion intensities of the deconvoluted peaks were used for quantification of the glycan species.

As shown in FIGS. 1-4 FIG. 7, monensin addition had a slight negative impact on cell growth and viability but these effects were not significant enough to cause any negative impact on the productivity of the cultures. In fact, monensin-treated tanks showed marginally improved titers as compared to the control tank. Importantly, addition of monensin led to a 9-10 fold increase in the levels of high mannose glycans on the recombinant antibodies (FIGS. 5-9). The primary increase was seen in Man5 species, though at earlier time points (days 9 and 10) other high order mannose species were also upregulated. From day 11 onwards, Man5 was almost the exclusive high mannose species present in the tanks with negligible quantities of other high mannose species detected.

Figure 9:
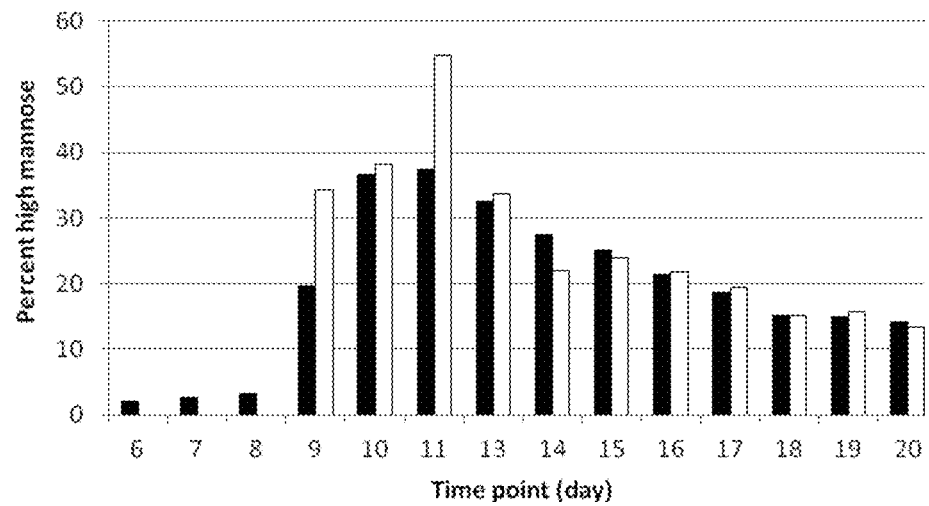
FIG. 9-12 depict the predicted and measured high mannose levels and the rate of high mannose decrease for MAb E produced in ATF reactors with monensin. Monensin concentration in ATF reactors Ra and Rb was held at 500 nM over the course of ~22 hours starting on day 8 and ending on day 9. For time-points when measured high mannose (black bars) was continuing to increase (days 9-11), predicted high mannose values (white bars) were calculated for Ra (FIG. 9) and Rb (FIG. 10) reactors based on the assumption that all of the produced MAb E antibodies contain high mannose glycans. For days 13 and on when high mannose levels on MAb E start decreasing, predicted high mannose values were calculated assuming that none of the newly produced MAb E antibodies contained any high mannose glycans (FIGS. 9 and 10). Fold titer increase (black bars) and fold high mannose decrease (white bars) were also calculated for this time period for Ra (FIG. 11) and Rb (FIG. 12).
Figure 10:
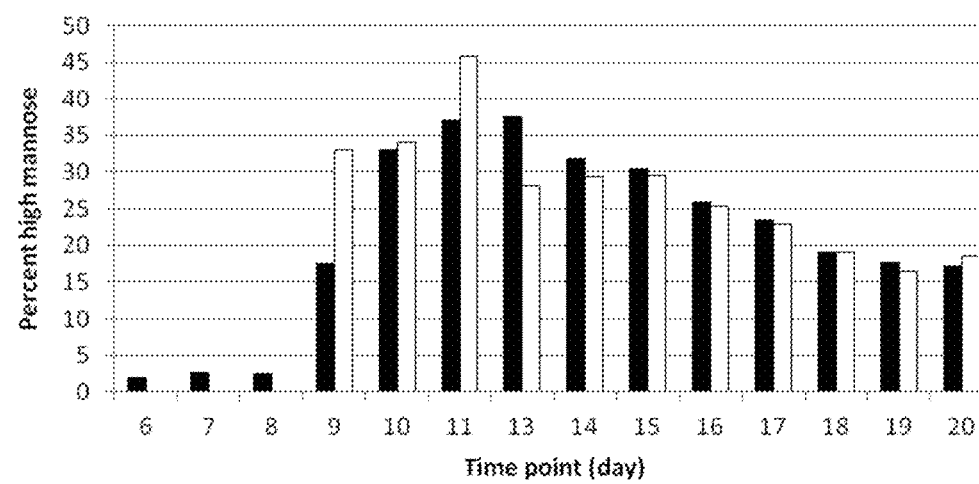
Figure 11:
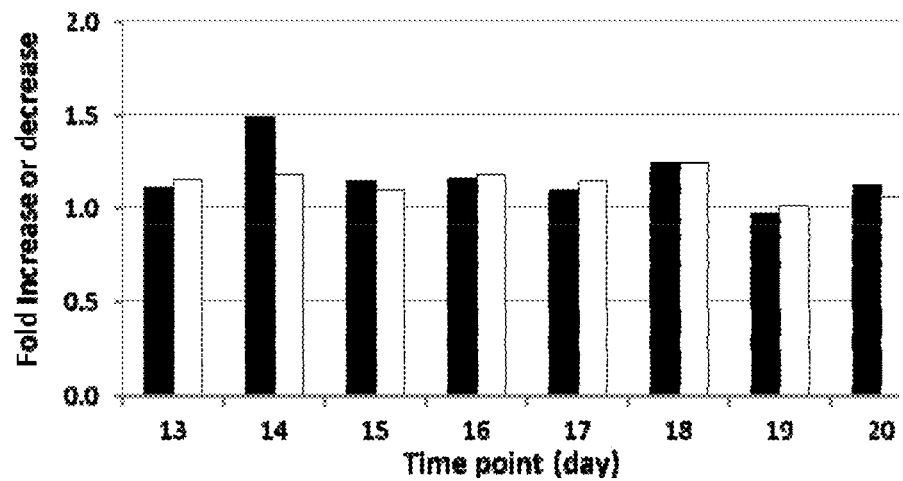
Figure 12:
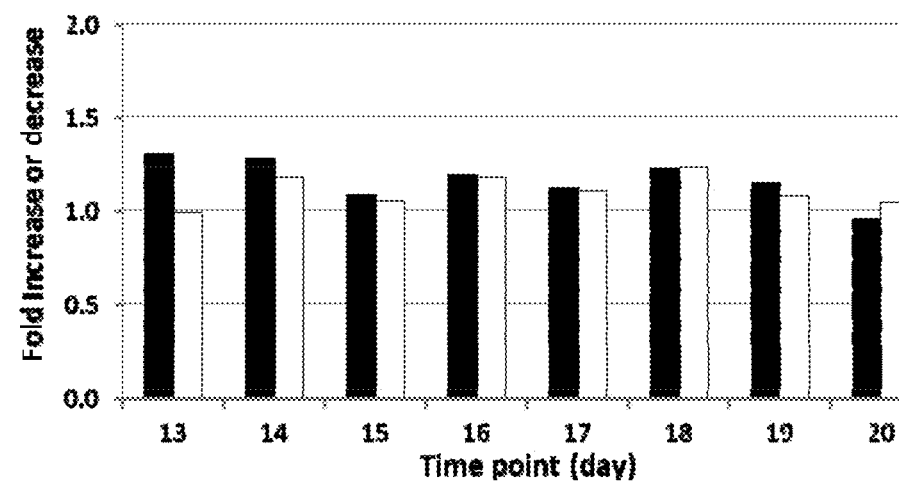

Comparisons of predicted and measured high mannose levels show that the expression of high mannose containing antibodies peaked on day 10 where 89% of the produced antibodies contained high mannose glycans (FIG. 9). Once monensin amounts became negligible in the tanks (based on perfusion medium flow rate calculations, days 11 and on), the rate of decrease in the percentage of antibodies with high mannose glycans was proportional to the rate at which the titer was increasing (FIG. 10). In other words, high levels of high mannose antibodies were diluted out with newly produced antibodies containing low level of high mannose.

Figure 13:
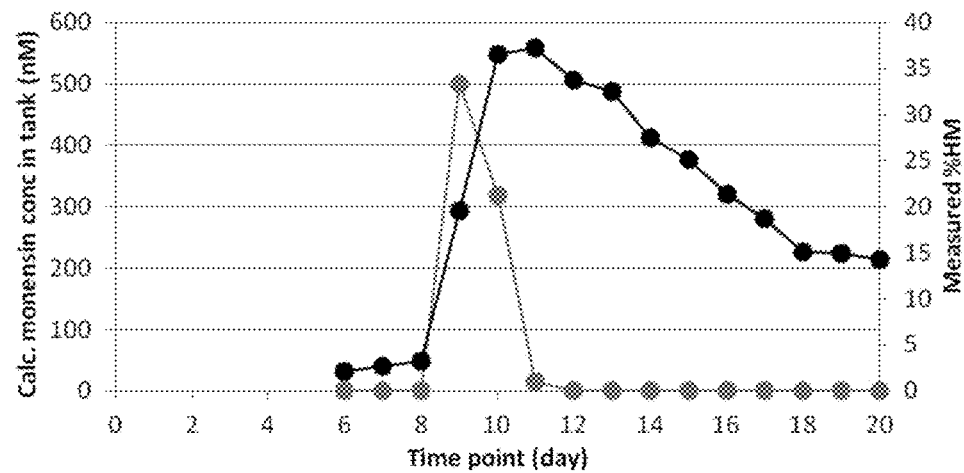
FIGS. 13 and 14 illustrate the calculated monensin concentration in ATF reactors Ra (FIG. 13) and Rb (FIG. 14). Monensin was bolused at 500 nM into reactors on day 8 and was maintained at that concentration for a period of ~22 hours. Monensin concentration in tanks after the termination of monensin administration was calculated based on the medium perfusion rates in the reactors (gray circles). Total measured percent high mannose is shown in black circles.
Figure 14:
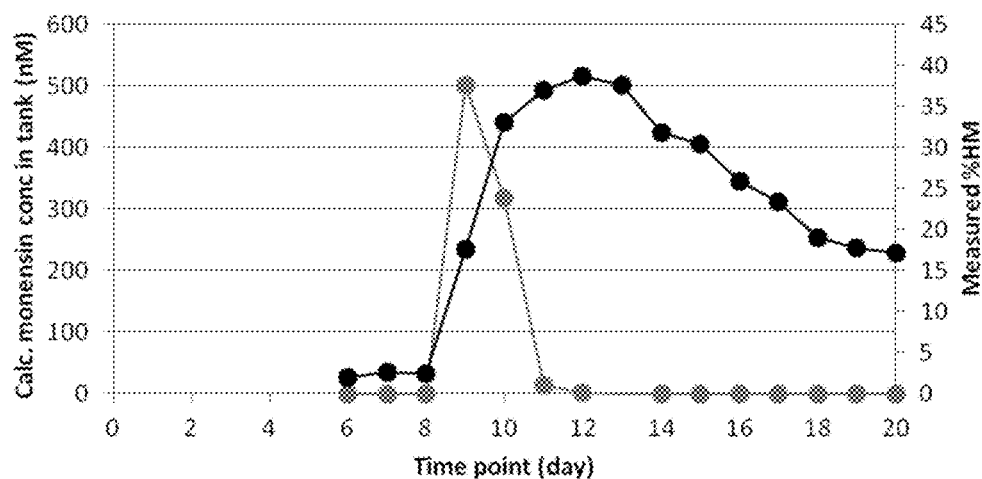

Overall, the increase in high mannose levels correlated well with the flow rate-based calculated concentrations of monensin in the tanks, with maximum increase seen on days 9 and 10 when monensin concentrations were at their highest and tapering down from day 11 onwards (FIGS. 9-12). After the complete flushing out of monensin from the tanks through the process of continuous medium perfusion, high mannose levels decreased from an initial spike of 35-50% down to 15-17% on the day of the harvest (FIGS. 13 and 14).

What is claimed is:

1. A method of regulating the high mannose denosumab glycoform content of a denosumab composition during a mammalian cell culture process, comprising:

establishing, in a serum-free culture medium in a bioreactor, a cell culture comprising genetically engineered CHO expressing denosumab, maintaining the CHO cells during a production phase, and adding monensin to said CHO cell culture during the production phase at a concentration of about 25 nM to about 500 nM, wherein the addition of monensin increases the high mannose denosumab glycoform content of the denosumab composition.

2. The method according to claim 1, wherein the amount of monensin is about 25 nM to about 200 nM.

3. The method of claim 2, wherein the monensin is added within about 0 to about 6 days from the start of the production phase of the cell culture.

4. The method of claim 3, wherein the monensin is added within about 0 to about 3 days from the start of the production phase of the cell culture.

5. The method of claim 1, wherein the monensin is added to the cell culture by addition of a perfusion medium containing the monensin, and wherein the concentration of monensin in the cell culture is maintained from about 25 nM to about 500 nM.

6. The method of claim 4, wherein the concentration of monensin maintained in the cell culture is from about 100 nM to about 500 nM.

7. The method of claim 2, further comprising the step of purifying denosumab from a mammalian cell culture.

8. The method of claim 7, wherein the purified denosumab is formulated into a pharmaceutically acceptable formulation.

9. The method of claim 4, further comprising the step of purifying denosumab from a mammalian cell culture.

10. The method according to claim 9, wherein the purified denosumab is formulated into a pharmaceutically acceptable formulation.

* * * * *